United States Patent
Ligler et al.

(10) Patent No.: US 9,157,060 B2
(45) Date of Patent: Oct. 13, 2015

(54) MICRO BLOOD VESSELS AND TISSUE DUCTS

(71) Applicants: Frances S. Ligler, Fuquay Varina, NC (US); André A. Adams, Burke, VA (US); Michael Daniele, Arlington, VA (US)

(72) Inventors: Frances S. Ligler, Fuquay Varina, NC (US); André A. Adams, Burke, VA (US); Michael Daniele, Arlington, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 242 days.

(21) Appl. No.: 13/784,216

(22) Filed: Mar. 4, 2013

(65) Prior Publication Data

US 2014/0087466 A1 Mar. 27, 2014

Related U.S. Application Data

(63) Continuation-in-part of application No. 13/081,688, filed on Apr. 7, 2011, now Pat. No. 8,398,935, which is a continuation-in-part of application No. 11/423,225, filed on Jun. 9, 2006, now Pat. No. 8,361,413.

(60) Provisional application No. 60/690,057, filed on Jun. 9, 2005.

(51) Int. Cl.
*C12N 5/071* (2010.01)
*B29D 99/00* (2010.01)
(Continued)

(52) U.S. Cl.
CPC .......... *C12N 5/0602* (2013.01); *B01J 19/0093* (2013.01); *B29D 99/0078* (2013.01); *G02B 6/032* (2013.01); *B01J 2219/0086* (2013.01); *B01J 2219/0093* (2013.01); *B01J 2219/00783* (2013.01); *B01J 2219/00831* (2013.01); *B01J 2219/00833* (2013.01); *B01J 2219/00873* (2013.01); *B01J 2219/00889* (2013.01); *B01J 2219/00891* (2013.01); *B01J 2219/00936* (2013.01); *B01L 3/502707* (2013.01); *B01L 3/502746* (2013.01); *B01L 3/502776* (2013.01);
(Continued)

(58) Field of Classification Search
CPC .............................. C12N 5/0068; C12M 29/16
USPC .................. 435/398, 400; 623/1.41, 1.54
See application file for complete search history.

(56) References Cited

U.S. PATENT DOCUMENTS 3,767,790 A * 10/1973 Guttag ........................... 424/479
5,855,608 A * 1/1999 Brekke et al. .................. 424/487
(Continued)

OTHER PUBLICATIONS

Boyd, D.A., A.R. Shields, J. Naciri, and F.S. Ligler "Hydrodynamic shaping, polymerization, and subsequent modification of thiol click fibers," ACS Appl. Mater. Interfaces, 2013, 5 (1), pp. 114-119.
(Continued)

*Primary Examiner* — Suzette J Gherbi
(74) *Attorney, Agent, or Firm* — US Naval Research Laboratory; Roy Roberts

(57) ABSTRACT

A fiber includes one or more layers of polymer surrounding a central lumen, and living animal cells disposed within the lumen and/or within at least one of the one or more layers, wherein the fiber has an outer diameter of between 5 and 8000 microns and wherein each individual layer of polymer has a thickness of between 0.1 and 250 microns. Also disclosed are model tissues including such fibers, and method of making such fibers. The fibers can serve as synthetic blood vessels, ducts, or nerves.

10 Claims, 34 Drawing Sheets

(51) Int. Cl.
*B01J 19/00* (2006.01)
*G02B 6/032* (2006.01)
*B01L 3/00* (2006.01)

(52) U.S. Cl.
CPC .. *B01L 2200/0636* (2013.01); *B01L 2400/0487* (2013.01); *B01L 2400/084* (2013.01); *G02B 2006/0325* (2013.01)

(56) References Cited

U.S. PATENT DOCUMENTS

| | | | |
|---|---|---|---|
| 8,398,935 B2 * | 3/2013 | Howell et al. | 422/503 |
| 2011/0250585 A1 | 10/2011 | Ingber et al. | |
| 2012/0193836 A1 * | 8/2012 | Sharma et al. | 264/465 |
| 2013/0312638 A1 * | 11/2013 | Parker et al. | 106/156.2 |

OTHER PUBLICATIONS

Chau, L.T., Rolfe, B.E., Cooper-White, J.J. 2011 A microdevice for the creation of patent, three-dimensional endothelial cell-based microcirculatory networks. Biomicrofluidics. 5(3).
Daniele MA, North SH, Naciri J, Howell PB, Foulger SH, Ligler FS, et al. "Rapid and continuous hydrodynamically controlled fabrication of biohybrid microfibers," Advanced Functional Materials. 2012, 23:6 698-704.
Date, A., et al. "Packaging Sensing Cells in Spores for Long-Term Preservation of Sensors" Anal. Chem., 2010, 82 (14), pp. 6098-6103.
Geckil H, Xu F, Zhang XH, Moon S, Demirci U. "Engineering hydrogels as extracellular matrix mimics," Nanomedicine (Lond) 2010; 5(3):469-484.
Gibbons MC, Foley MA, O'Halloran-Cardinal K. "Thinking inside the box: Keeping tissue-engineered constructs in vitro for use as preclinical models. Tissue Engineering: Part B,". 2012;19(1):17.
Hoyle et al., "Thiol Click Chemistry," Chem. Soc. Rev., 2010,39, 1355-1387.
Huh, D; Ingber et al., Reconstituting organ-level lung functions on a chip, Science, 2010, 328, 1662.
Jang, K.-J., and Suh, K.-Y. "A multi-layer microfluidic device for efficient culture and analysis of tubular cells." Lab on a Chip (2010) 10, 36-42.
Kaushal, S., Amiel, G.E., Guleserian, K.J., Shapira, O.M., Perry, T., Sutherland, F.W., et al. 2001 Functional small-diameter neovessels created using endothelial progenitor cells expanded ex vivo. Nat Med. 7(9):1035-40.
Langer, R., Vacanti, J.P. 1993 Tissue Engineering. Science. 260(5110):920-6.
Levenberg, S., Rouwkema, J., Macdonald, M., Garfein, E.S., Kohane, D.S., Darland, D.C., et al. 2005 Engineering vascularized skeletal muscle tissue. Nat Biotechnol. 23(7):879-84.
Liu, Y.X. Markov, D.A., Wikswo, J.P., Mccawley, L.J. 2011 Microfabricated scaffold-guided endothelial morphogenesis in three-dimensional culture. Biomed Microdevices. 13(5):837-46.
Lutolf MP, Hubbell JA. "Synthetic biomaterials as instructive extracellular microenvironments for morphogenesis in tissue engineering," Nature Biotechnol. 2005;23(1):47-55.
Nichol, J.W., Koshy, S.T., Bae, H., Hwang, C.M., Yamanlar, S., Khademhosseini, A. 2010 Cell-laden microengineered gelatin methacrylate hydrogels. Biomaterials. 31(21):5536-44.
Niklason, L.E., Gao, J., Abbott, W.M., Hirschi, K.K., Houser, S., Marini, R., et al. 1999 Functional arteries grown in vitro. Science. 284(5413):489-93.
Shields, A.R., A.L. Thangawng, C.M. Spillmann, J. Naciri, P.B. Howell, and F.S. Ligler (2012) "Hydrodynamically directed multiscale assembly of shaped polymer fibers," Soft Matter 8, 6656-6660.
Shuler, M.L. 2012 Modeling Life. Ann Biomed Eng. 40(7):1399-1407.
Thangawng, A.L., P.B. Howell, C.M. Spillman, J. Naciri, and F.S. Ligler (2011) "UV polymerization of hydrodynamically shaped fibers," Lab Chip 11, 1157-1160.
Thangawng, A.L., P.B. Howell, J.J. Richards, J.S. Erickson, and F.S. Ligler (2009) "A simple sheath-flow microfluidic device for micro/nanomanufacturing: fabrication of hydrodynamically shaped polymer fibers," Lab Chip 9, 3126-3130.
Van Der Meer, A.D., Van Den Berg, A. 2012 Organs-on-chips: breaking the in vitro impasse. Integr Biol-Uk. 4(5):461-470.
Wong, K.H.K., Chan, J.M., Kamm, R.D., Tien, J. 2012 Microfluidic Models of Vascular Functions. Annu Rev Biomed Eng. 14:205-230.

\* cited by examiner

MICRO BLOOD VESSELS AND TISSUE DUCTS

CROSS-REFERENCE TO RELATED APPLICATIONS

This application is a Continuation-In-Part of U.S. patent application Ser. No. 13/081,688 filed on Apr. 7, 2011, which in turn is a Continuation-In-Part of U.S. patent application Ser. No. 11/423,225 filed on Jun. 9, 2006 (now U.S. Pat. No. 8,361,413), which claims the benefit of U.S. Provisional Patent Application Ser. No. 60/690,057 filed on Jun. 9, 2005. This application is also related to U.S. patent application Ser. Nos. 12/987,251 and 13/728,651, filed on Jan. 10, 2011 and Dec. 27, 2012, respectively. Each of these applications is incorporated herein by reference.

BACKGROUND

Sheath flow is a widely used technique for a variety of applications, including but not limited to particle counting, flow cytometry, waveguiding, and fluid control. Sheath flow involves surrounding a central flow stream (the core) with a surrounding stream (the sheath). In particle counting and flow cytometry applications, the sheath prevents particles in the core from coming into contact with the walls of the channel, thus preventing adhesion and clogging. The sheath also serves to focus the particles or molecules into the center of the channel, allowing for easy counting or measurement through optical or other means. Sheath flow is normally laminar flow that substantially avoids mixing between the core stream and the sheath stream. Sheath flow can also be used with fluids of different refractive index to create a waveguide in the core or sheath stream in order to measure transfer of analytes from one stream to the other or to control the rate of interaction between molecules in one or both streams for carefully controlled chemistry or analysis.

Previous designs have created sheath flow through an annular arrangement. A small nozzle was positioned inside a larger tube. The core solution was pumped through the nozzle and the sheath solution was pumped through the larger tube. This configuration required careful alignment of the two tubes and did not easily lend itself to miniaturization. Since the diameter of the nozzle was fixed, the relative sizes of the core stream and sheath solution were relatively constant within a set range.

Other devices provide sheath flow on a chip, but the flow typically operates only in two dimensions. The core stream in these devices is bordered on either side by the sheath streams, however the core is not sheathed top and bottom. The complexity of the support plumbing for these devices is increased, as the number of flow streams is increased from two to three as compared to the annular arrangement design. It is possible to sheath the stream on the top and bottom of the core stream in these systems by adding two additional inlet ports in the top and bottom of the channel. However, this greatly increases the manufacturing complexity of the device. Micromachining technologies are inherently two-dimensional. Three-dimensional channel paths can be created by stacking several two dimensional designs on top of one another, but this adds to the complexity and difficulty of the manufacturing process. Creating a fully sheathed flow in this way could require at least several individual levels, which must be independently produced and then carefully aligned. In addition, use of the device could require multiple pumps to provide solutions to all the inlets.

Tissue Engineering

Studying the growth and differentiation of cells in culture in the presence of various nutrients and growth factors has provided physiologically relevant information about how the corresponding cells function in vivo. Classic tissue engineering mixes cell types with different growth factors and provides minimal control over morphology and microanatomy [Langer, R., Vacanti, J. P. 1993 "Tissue Engineering." *Science.* 260(5110):920-6; Levenberg, S., Rouwkema, J., Macdonald, M., Garfein, E. S., Kohane, D. S., Darland, D. C., et al. 2005 "Engineering vascularized skeletal muscle tissue." *Nat Biotechnol.* 23(7):879-84.]. It is becoming increasingly clear that cell differentiation and function are impacted by fluid flow, proximity of other cell types, and substrate geometry. The realization of the importance of such factors has motivated the microfluidics and tissue engineering communities to create "tissue-on-chip" or "organ-on-chip" model systems that can introduce methods for controlling such variables and provide more complex in vitro systems for the study of normal differentiation and pathogenesis or drug metabolism and transport (Wong, K. H. K., Chan, J. M., Kamm, R. D., Tien, J. 2012 Microfluidic Models of Vascular Functions. *Annu Rev Biomed Eng.* 14:205-230; Van Der Meer, A. D., Van Den Berg, A. 2012 "Organs-on-chips: breaking the in vitro impasse." *Integr Biol-UK* 4(5):461-470; Shuler, M. L. 2012 "Modeling Life." *Ann. Biomed. Eng.* 40(7):1399-1407).

In general, these tissue-on-chip models are configured with one of two types of architectures. For decades, investigators have been configuring substrates to have a specific geometry that will impact cell differentiation, most notably defining surface topography or creating channels to direct cell growth. In both cases, the cells are introduced after the substrate is configured, and cells adhere to defined portions of the substrate. Surface patterning of endothelial or progenitor cells has been used to engineer blood vessels [Niklason, L. E., Gao, J., Abbott, W. M., Hirschi, K. K., Houser, S., Marini, R., et al. 1999 "Functional arteries grown in vitro." *Science.* 284(5413):489-93; Kaushal, S., Amiel, G. E., Guleserian, K. J., Shapira, O. M., Perry, T., Sutherland, F. W., et al. 2001 "Functional small-diameter neovessels created using endothelial progenitor cells expanded ex vivo." *Nat Med.* 7(9):1035-40.]. Chip-based approaches to generating engineered blood vessels pattern layers of cells onto tubular or rectangular microchannels to emulate blood vessel geometry; however, these methods do not produce a free-standing engineered blood vessel. The microchannel-attached engineered blood vessel does not allow for superfusion along the blood vessel wall or branching from the main vessel. [Nichol, J. W., Koshy, S. T., Bae, H., Hwang, C. M., Yamanlar, S., Khademhosseini, A. 2010 "Cell-laden microengineered gelatin methacrylate hydrogels." *Biomaterials.* 31(21):5536-44. Chau, L. T., Rolfe, B. E., Cooper-White, J. J. 2011 "A microdevice for the creation of patent, three-dimensional endothelial cell-based microcirculatory networks." *Biomicrofluidics.* 5(3); Liu, Y. X., Markov, D. A., Wikswo, J. P., Mccawley, L. J. 2011 "Microfabricated scaffold-guided endothelial morphogenesis in three-dimensional culture." *Biomed Microdevices.* 13(5):837-46.] More recently, porous membranes have been suspended across a microfluidic well or channel and cells grown on one or both surfaces of the porous membrane. The cells generally form monolayers while air or liquids are flowed above and/or below the membrane (for example, U.S. Patent Application Publication No. 2011/0250585A1 and Huh, D, Ingber et al., "Reconstituting organ-level lung functions on a chip," *Science,* 2010, 328, 1662.). Both of these approaches limit the tissue-on-chip construct to planar configurations for the resulting cell organizations. The depth of the cell layers in planar tissue models is constrained by the need to transport nutrients and growth factors from the fluid in the microfluidic channel, preventing the formation of thick tissues.

In nature, the transport of nutrients, growth factors, protective molecules, and waste are provided by the vasculature and other types of ducts. Cells including both those that provide immunity and oxygenation and those that cause infection, autoimmune disease and cancer are also transported through the vasculature. The need for tubular structures to incorporate into tissue-on-chip models is recognized (e.g. Wong et al., ibid.). Ideally, such vasculature would be round as in nature, flexible to accommodate complex organ geometries, and composed of a biocompatible or biodegradable material that can be remodeled by the incorporated cells (not polydimethylsiloxane). The roadblock to vascularized tissue models is twofold: (1) accurate fabrication of engineered blood vessels and (2) integration of engineered blood vessels into on-chip models.

In the present state of the art, elongated blood vessel structures require either cells grown in channels [Franco, C., Gerhardt, H. 2012 "Tissue Engineering: Blood vessels on a chip." *Nature.* 488(7412):465-6.], cells seeded onto preformed scaffolds, or cultures using blood vessels excised from animals [Quint, C., Kondo, Y., Manson, R. J., Lawson, J. H., Dardik, A., Niklason, L. E. 2011 "Decellularized tissue-engineered blood vessel as an arterial conduit." *Proc. Nat'l Acad. Sci. USA.* 108(22):9214-9.]. The first methods do not provide stand-alone blood vessels and culturing excised vessels is not a viable source for producing cost and time-effective human tissue models. Production of collagen-based blood vessel scaffolds for subsequent cell incorporation is already being used clinically, where it is desirable for the patient to provide his own cells. However, these scaffolds are large and replace veins or arteries rather than capillaries. The scaffold structures are generally millimeters in diameter, and nutrient availability in vitro might limit cells to growth near the surface of the scaffold, making them less appropriate for tissue-on-chip models. Development of methods for producing blood vessels to operate and supply tissue models would provide a much more accurate model for blood delivery to tissue and provide for growth of on-chip tissues in three dimensions.

The range of applications for the nano- and microfabrication of cell-laden and/or coated tubular constructs are not limited to vasculature. Directed nerve growth has been shown whereby neurons are seeded into scaffolds composed of poly L-lactic acid nanofibers. [F. Yang, R. Murugan, S. Ramakrishna, X. Wang, Y.-X. Ma, S. Wang, "Fabrication of nano-structured porous PLLA scaffold intended for nerve tissue engineering," *Biomaterials* 25 (2004) 1891-1900]. The scaffolds initiated axonal guidance, which was postulated as a first step in bridging the gaps between the proximal and distal nerves that do not close during healing. An inkjet printing station for neuroregenerative tissue engineering was presented by Silva, D. S., D. B. Wallace, et al. (2007) [IEEE Dallas Engineering in Medicine and Biology Workshop: 71-73]. The resulting tubes were seeded with neurons and served as scaffolds that resulted in significant outgrowth.

Ductal tissues play essential roles in human physiology by providing conduits that facilitate the transfer of fluids such as seminal fluid, bile, and milk. These conduits serve as the interfaces between exocrine glands and distal regions both internal and external. Ducts differ from blood vessels in that they are often not simply passive conduits, but actively participate in the secretions that facilitate the expelling of waste or transfer of reproductive materials. As an example, a multilayer microfluidic device that was used to culture and analyze renal tubule cells [Jang, K.-J., and Suh, K.-Y. "A multilayer microfluidic device for efficient culture and analysis of tubular cells." *Lab on a Chip* (2010) 10, 36-42]. A fibronectin-coated polyester membrane was inserted between the layers of a polydimethylsiloxane (PDMS) microfluidic channel, and primary kidney cells were introduced on one side. During culture, the membrane was subjected to continuous shear stress of 1 dyn/cm$^2$ for 5 h. The cells formed a layer on the polyester membrane and developed markers typical of renal tubule cells.

In view of the above, a need exists for the engineering of blood vessels, tissue ducts, and the like having physiologically-appropriate shapes, dimensions, and properties. Most prior methods for making polymer fibers involve conditions that are not compatible with living cells, in that they typically involve elevated temperature, high sheer, organic solvents, or combinations of these. Techniques described herein provide a biocompatible method for making shaped polymer fibers using hydrodynamic focusing.

BRIEF SUMMARY

A fiber comprises one or more layers of polymer surrounding a central lumen, and living mammalian cells disposed within the lumen and/or within at least one of the one or more layers, wherein the fiber has an outer diameter of between 5 and 8000 microns and wherein each individual layer of polymer has a thickness of between 0.1 and 250 microns. The fibers is in a condition of having been generated via sheath flow. The lumen is optionally hollow or filled with a polymer.

Another embodiment is a model tissue comprising an inlet port and an outlet port, and at least one fiber comprising: one or more layers of polymer surrounding a central lumen, and living mammalian cells disposed within the lumen and/or within at least one of the one or more layers, wherein the fiber has an outer diameter of between 5 and 8000 microns and wherein each individual layer of polymer has a thickness of between 0.1 and 250 microns, and wherein the fiber is in a condition of having been generated via sheath flow.

A further embodiment is a method of generating a fiber by creating a sheath flow comprising a core stream surrounded by one or more sheath streams, wherein at least one of the core or sheath streams comprises a polymerizable material and wherein at least one of the core or sheath streams comprises living mammalian cells; and polymerizing the polymerizable material to form a fiber wherein the fiber comprises: one or more layers of polymer derived from the one or more sheath streams surrounding a central lumen derived from the core stream, and the living mammalian cells disposed within the lumen and/or within at least one of the one or more layers, wherein the fiber has an outer diameter of between 5 and 8000 microns and wherein each individual layer of polymer has a thickness of between 0.1 and 250 microns. In the sheath flow, the polymerizable material and the cells may be located in the same or different streams.

BRIEF DESCRIPTION OF THE DRAWINGS

FIG. 21B shows a fiber run at the 2500:1 ratio which split into two filaments that hardened as independent, but parallel filaments.

FIG. 22A shows the model results on the z and y axes while FIG. 22B shows a perspective view generated by the model.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a," "an," and "the" do not preclude plural referents, unless the content clearly dictates otherwise.

As used herein, the term "and/or" includes any and all combinations of one or more of the associated listed items.

As used herein, a "core" refers to a fluid flow that is concentrically surrounded by another fluid flow, termed the "sheath." Together the core and sheath flow are referred to as a "sheathed flow." A core may optionally include within it an interior core, so that the interior core surrounded by an exterior portion of the core serving as a sheath. Optionally, the interior core may in turn serve as a sheath to a deeper interior core, and so on. The cores may have differing compositions. As used herein, the term "simple core" refers to a core lacking an interior core.

As used herein, the term "cross-section" refers to cross-sectional shape, area, and/or dimension(s).

Description

In the present device and method, one or more core streams and one or more sheath streams are introduced into a single channel. One or more fluid transporting structures located at the top and bottom of the channel direct the sheath fluid around the core stream, separating the core stream from the walls of the channel. Once the position of the core stream is established in the interior of the channel, it remains in that position due to laminar flow.

Figure 1:
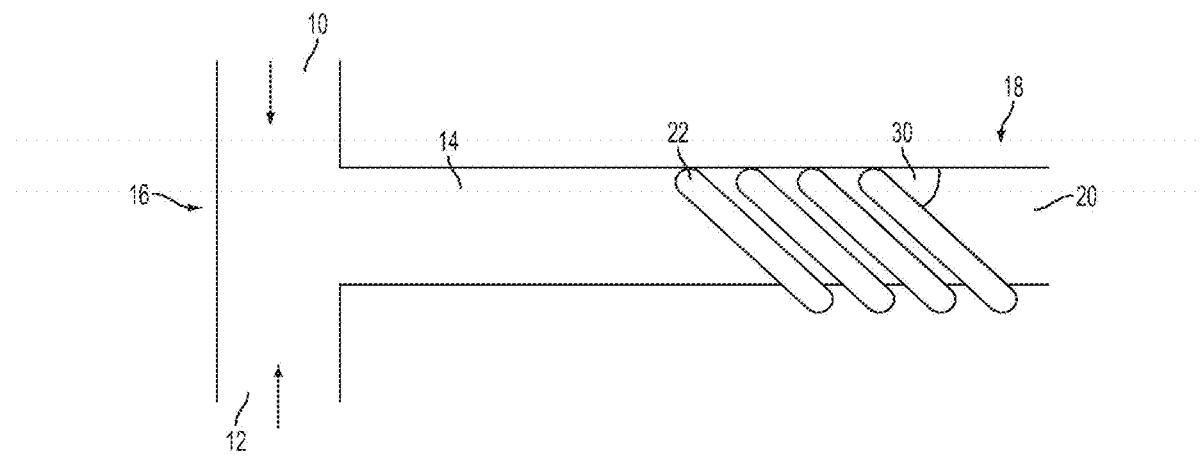
FIG. 1 is a view of one example of a sheath flow device.

FIG. 1 shows a top view of one example of a sheath flow device. A sheath stream inlet 10, and a core stream inlet 12, allow a sheath stream and a core stream to be introduced into a channel 14. One design provides for a at a 'T' intersection at the proximal end 16 of the channel 14. The sheath stream and the core stream flow down the channel side-by-side towards the distal end of the channel 18 where an outlet 20 is present. At least one fluid transporting structure 22 such as a groove or a ridge is located in the channel 14 between the inlets 10, 12 and the outlet 20. The fluid transporting structure 22 transports the sheath stream across the top and bottom of the channel 14 to completely surround the core stream. The fluid transporting structure 22 crosses the channel 14 at an angle 30.

The device can be readily fabricated using a variety of techniques, including molding, milling, laser ablation, soft lithography techniques and other fabrication techniques known to those skilled in the art. Any material that can be machined or molded into the appropriate shapes can be used. The current techniques used in the mass production of microfluidic components can be easily adapted to the production of this sheath flow design.

Figure 2:
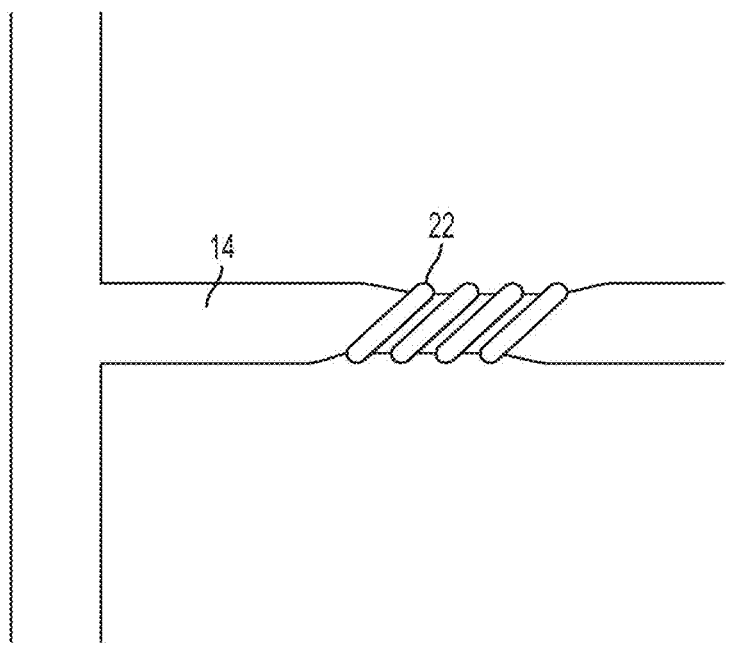
FIG. 2 is a view of one example of a sheath flow device.

The exact shape of the channel is not critical. For example, FIG. 2 shows a channel 14 with a constriction at the location of the grooves 22. The constricted device showed similar behavior to devices without the constriction. The size of the channel can be varied within a broad range of size scales. The size of the channel is limited at the lower end by diffusion. When the width or diameter of the channel reaches the diffusional distance of the molecules or particles of interest, any attempts to confine them to a specific region of the channel will be thwarted.

The upper limit for the channel width is set by the Reynolds number of the system. The device shown in FIG. 1 has been shown to function at Reynolds numbers up to and including 200. This means that the device can be fabricated into larger sizes using slower velocities or higher viscosity fluids. Sheath flow devices have been fabricated for use with high viscosity fluids that are 3 mm in width that have Reynolds numbers of 0.0008, so the actual channel diameter can be significantly wider than that with the use of appropriate fluids. The device will operate at Reynolds numbers up to those at which turbulence is initiated.

The channel has at least two inlets at or near its proximal end. The inlets are used to introduce a sheath stream and a core stream into the channel. The size and exact location of the inlets are can be varied, provided that the fluid transporting structure in the channel is located downstream from the inlets.

The at least one fluid transporting structure is typically a groove or a ridge located inside the channel. The structure transports the sheath stream laterally across the channel and around the core stream, separating the core stream from the walls of the channel. Once the position of the core stream is established in the interior of the channel, it remains in that position due to laminar flow. The angle of the fluid transporting structure across the channel is not necessarily critical to the design, however it has been found to be important in applications involving shaping of the core. FIG. 1 shows a device having a fluid transporting structure 22 that has an angle 30 that is about 45° relative to the channel; however, other oblique angles will work as well.

Figure 19A:
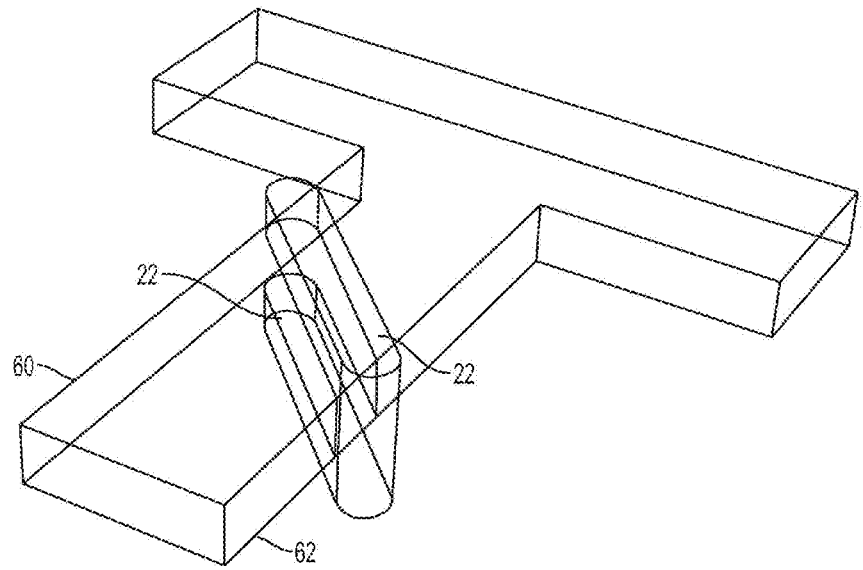
FIG. 19a is view of one example of a sheath flow device showing fluid transporting structure across the top surface and a second fluid transporting structure across the bottom surface.
Figure 19B:
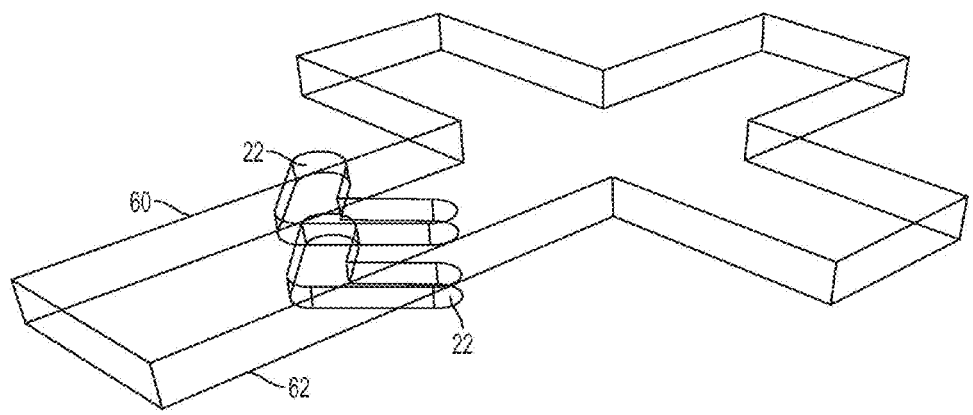
FIG. 19b is view of one example of a sheath flow device showing fluid transporting structure across the top surface and a second fluid transporting structure across the bottom surface.

The number and depth of the fluid transporting structures are design parameters that also can be adjusted to suit particular applications. A single structure located on the top and bottom of the channel will provide for a full sheath around the core stream. The grooves do not have to be precisely aligned along the flow axis in order for the device and method to operate. However, their lateral alignment may be important. Increasing the number of fluid transporting structures provides control over the lateral position of the core within the channel. Increasing the size of the fluid transporting structures correlates with a more effective transport of the sheath stream across the channel. Preferably, the fluid transporting structures penetrate the wall of the channel on the downstream end. FIG. 1 shows the fluid transporting structures 22 penetrating the wall of the channel 14 on the downstream end. This penetration increases the effectiveness of the fluid transport to better encase the core stream in the sheath stream. Sheathing will occur, however, even if the fluid transporting structure does not penetrate the channel wall. FIGS. 19a and 19b show a two embodiments of the present sheath flow device having a first fluid transporting structure 22 located across a top surface 60 of a channel and a second fluid transporting structure 22 located across a bottom surface 62 of a channel.

Figure 3A:
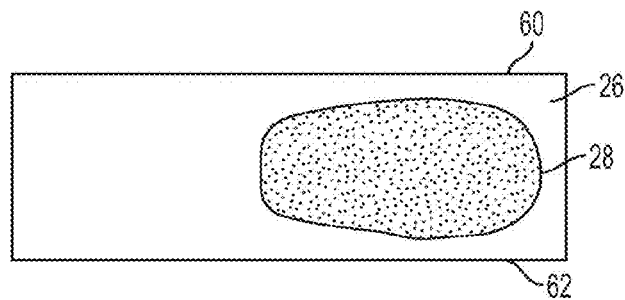
FIGS. 3A through 3F show a series of representative cross sections of sheathed flow.
Figure 3B:
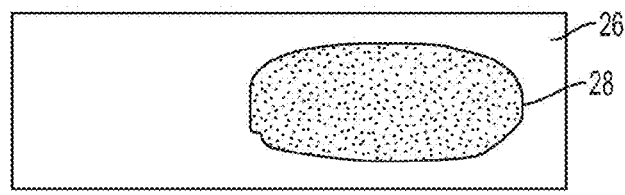
Figure 3C:
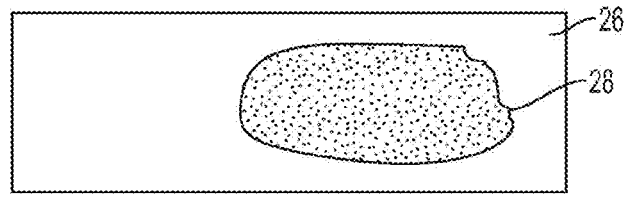
Figure 3D:
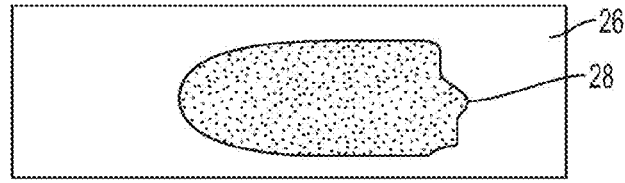
Figure 3E:
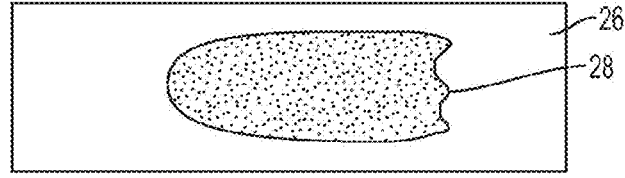
Figure 3F:
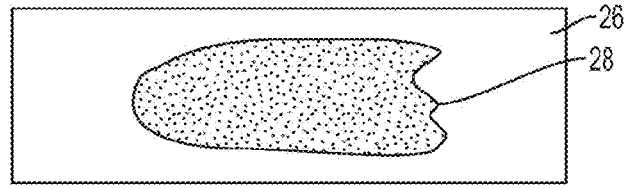

Example: The number of grooves can be used to control the position of the core within the channel. FIGS. 3(a) through 3(f) show the cross-sections resulting from a sheath flow device having 1 pair of grooves through 6 pairs of grooves, respectively. One pair of grooves is sufficient to completely surround the core stream 28 with sheath stream 26. FIG. 3(a) illustrates the top surface 60 of the channel and the bottom surface 62 of the channel. Subsequent pairs carried more sheath fluid to the right, causing the core to be shifted leftward. Having four pairs of grooves appears to be sufficient to place the core roughly in the center of the channel. Depending on the relative flow rates of the two fluids, the core can be made as small as 1% of the total channel cross-section. It is also possible to make the core quite large without losing the sheathing effect.

Figure 4:
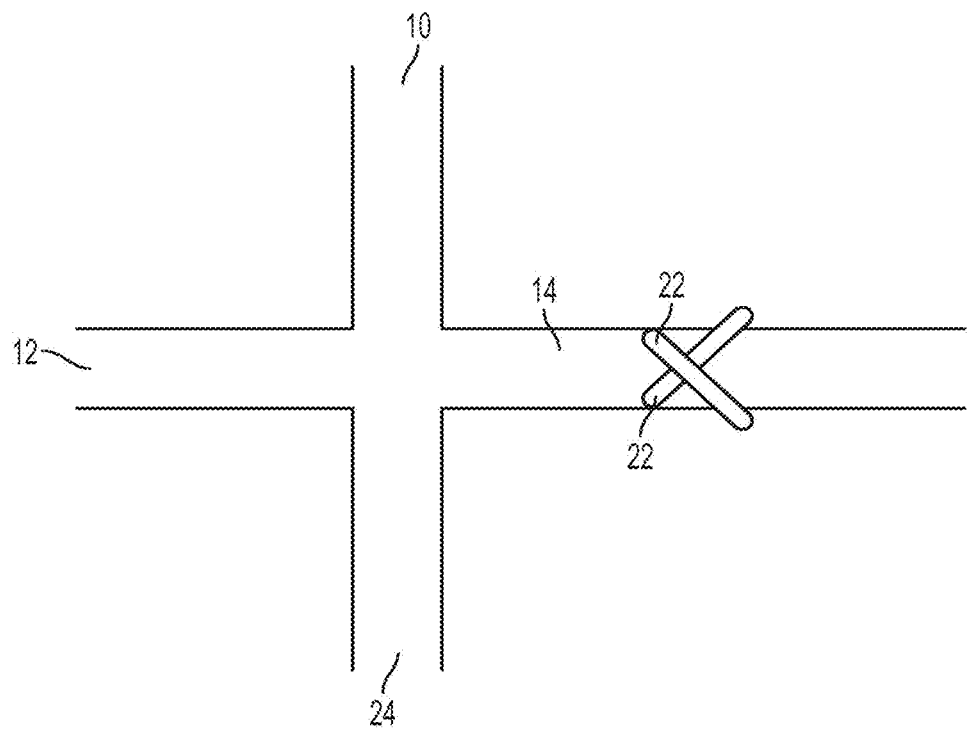
FIG. 4 is a view of one example of a sheath flow device.

The fluid transporting structures may also be used in a cross configuration when sheath solution is provided from both sides by a third inlet. FIG. 4 shows a channel, 14, having a first sheath stream inlet 10 and a second sheath stream inlet 24. The core stream inlet 12 is located between the first and second sheath stream inlets. A first groove 22 located in the top of the channel moves sheath stream from the left of the channel across the top. An opposing groove 22 located at the bottom the channel in a cross configuration with the first groove moves solution from the right of the channel across the bottom. This design has the advantage that the centroid of the core remains stationary, even when the relative flow rate of the core solution is varied. Additionally, the first and second sheath stream inlets allow differing sheathing materials to be introduced into the channel.

Figure 5:
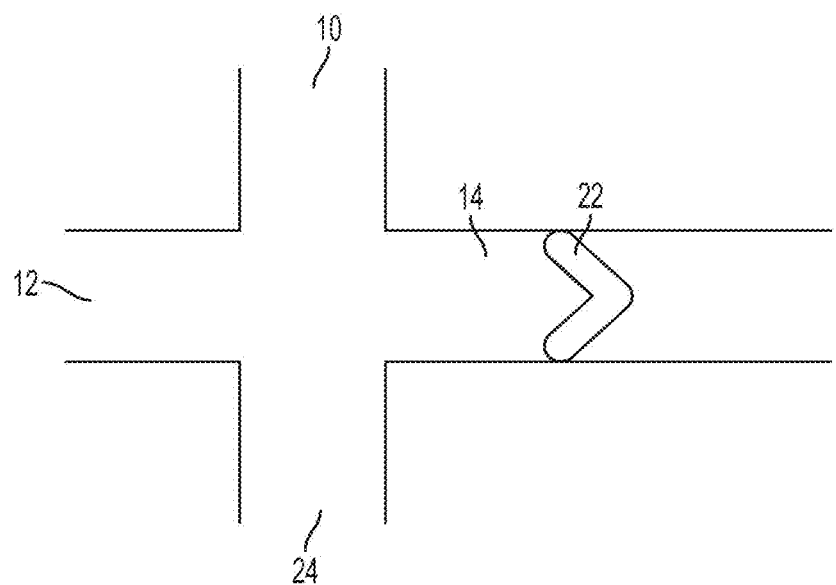
FIG. 5 is a view of one example of a sheath flow device.

Further, the fluid transporting structures located on the top and bottom of the channel may be configured in a shape that crosses the channel having a central area that is distal to its ends, as show in FIG. 5. The fluid transporting structure 22 of FIG. 4 is shown as a "v" shape, however, any shape having a central area that is located distally in the channel to its ends would work, such as a semi-circle. FIG. 4 shows a channel, 14, having a first sheath stream inlet 10 and a second sheath stream inlet 24. The core stream inlet 12 is located between the first and second sheath stream inlets. Fluid transporting structures 22 located in the top of the channel moves sheath stream across the core stream to sheathe the core stream.

Example: A microfluidic chip was made using a Technoisel CNC milling router (Techno Inc., New Hyde Park, N.Y.) in poly(methylmethacrylate) (PMMA) (Plexiglas G, Atofina Chemical Inc., Philadelphia, Pa.) via a method described by Howell, et al, Lab on a Chip 2005, 5, 524-530, Howell, et al, Lab on a Chip 2004, 4, 663-669, and Mott, et al, Lab on a Chip 2006, 6, 540-549, all incorporated in full herein by reference. The main channel was 3.18 mm wide by 1.02 mm deep. The grooves were 0.794 mm wide by 0.51 mm deep, and placed in pairs on both the top and bottom of the channel. A 70% fructose solution was used as core and the sheath solutions to ensure that the flow within the channel stayed in the Stokes regime. The sheath stream was labeled with fluorescent dye (Rhodamine W T, Bright Dyes, Miamisburg, Ohio). Channel cross-sections downstream of the grooves were obtained via a method described previously by Howell, P. B. et al, Lab on a Chip 2005, 5, 524-530 and Mott, et al, Lab on a Chip 2006, 6, 540-549, both incorporated in full herein by reference.

Figure 6:
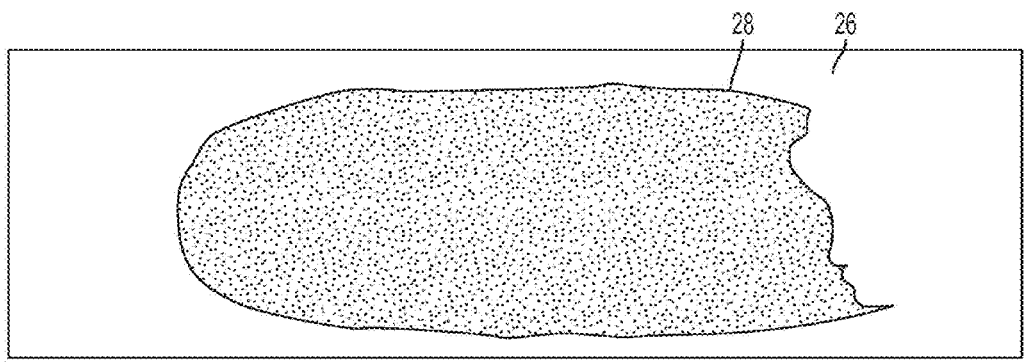
FIG. 6 is a representative cross section of sheathed flow.
Figure 7:
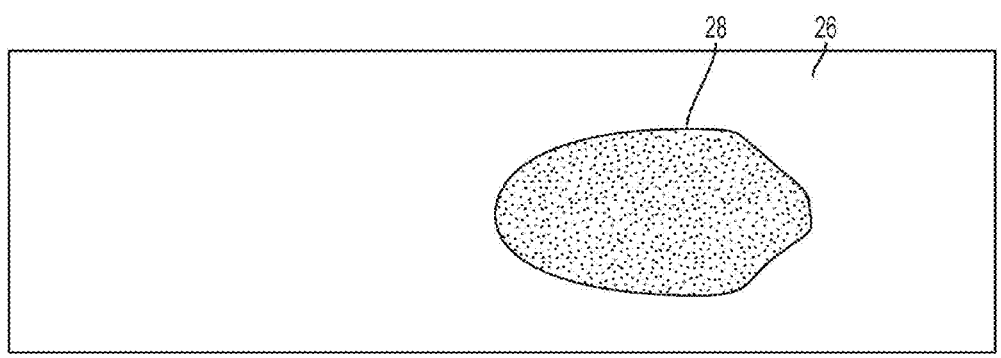
FIG. 7 is a representative cross section of sheathed flow.

The relative flow rate of the two streams can be widely varied without compromising the integrity of the sheath. FIG. 6 demonstrates a core-to-sheath ratio of 4:1. While the volumetric flow rate of the sheath stream 26 constitutes just 20% of the channel, it still completely surrounds the core stream 28. FIG. 7 demonstrates that a core-to-sheath ratio of 1:4. While the core stream 28 has been reduced to 20% of the net flow compared to the sheath stream 26, it is still clearly defined. For the specific device and method used in the example, a stable, fully enveloped sheath flow for Reynolds numbers of up to approximately 200 was generated before the limits of the pump were reached.

Figure 8:
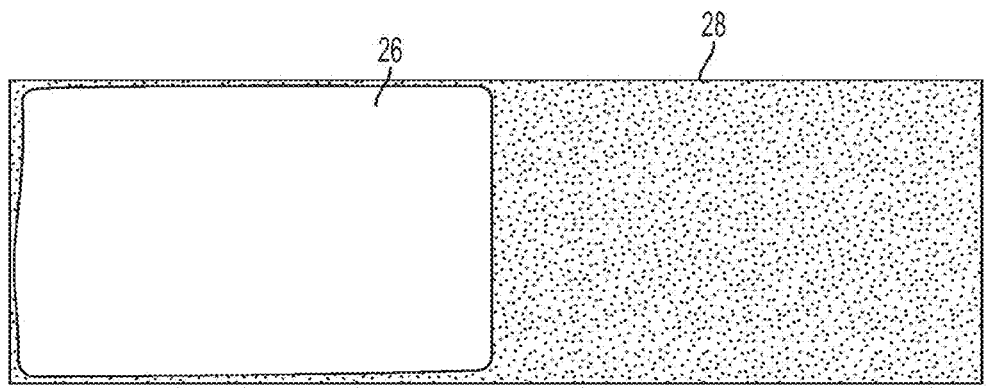
FIG. 8 is a representative cross section of sheathed flow.
Figure 9:
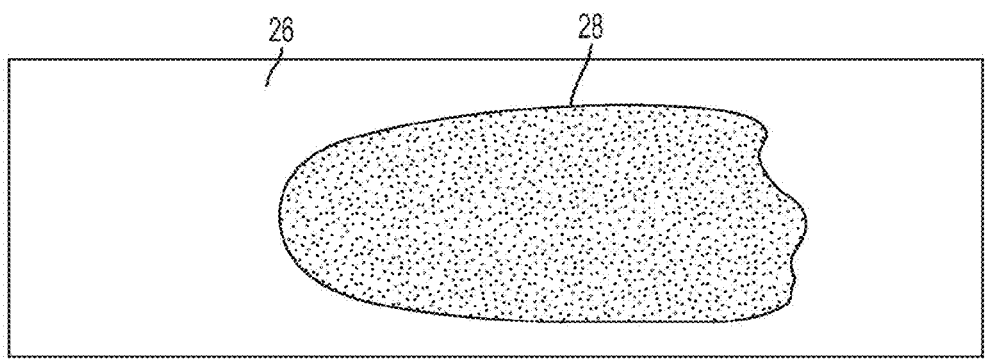
FIG. 9 is a representative cross section of sheathed flow.
Figure 10:
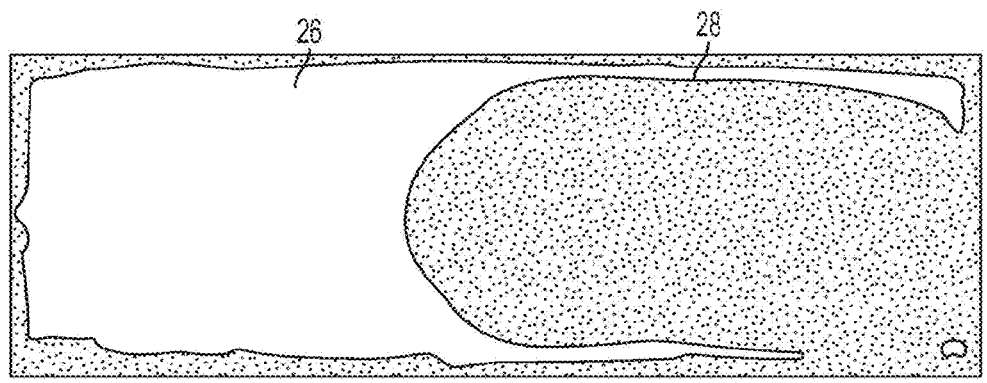
FIG. 10 is a representative cross section of unsheathed flow.

FIG. 8 shows a typical cross-section of the channel before sheathing. Sheath stream 26 and core stream 28 are side by side in the channel. FIG. 9 shows the sheath stream 26 surrounding the core stream after passing the fluid transporting structures, not shown. Fluorescent dye can be added to either the sheath stream or the core stream to provide contrast. Unlike other sheath flow systems, this device has also been shown to be reversible. It is possible to unsheathe a sheathed flow to recapture both the core and the sheath with high efficiency. Unsheathing is achieved by providing a second fluid transporting structure located proximally in the channel from the first fluid transporting structure. The second fluid transporting structure is arranged with a reversal of direction as compared to the first fluid transporting structure. The second fluid transporting structure does not have to be arranged to be the exact reverse of the first fluid transporting structure, however, the orientation is in the opposite direction from the first. The ability to unsheathe a sheathed flow can be useful in systems where the sheath solution is in limited supply and the capability of recycling the flow is advantageous, such as continuous monitoring on a space station or other enclosed environment. It would also be useful where the solute or particles in the core solution were very precious and recapture is important. FIG. 10 shows the sheath stream 26 and the core stream 28 after unsheathing.

The diameters of the sheath and core can vary widely depending on the intended use of the device. FIGS. 8-10 show cross sections of a sheath flow system where the flow rate of the sheath stream is approximately the same as that of the core fluid and the sheath and the core have similar cross sectional areas. FIGS. 11 a-c show systems in which the relative flow rates of the core stream 28 and sheath stream 26 are adjusted so that the core diameter is very small compared to the sheath (<16 micron core compared to 3 millimeters sheath).

Using specific variations in the pattern of grooves, the exact location of the core stream can be also be moved across the channel. The capacity either to separate the walls of the channel from the core fluid using a minimum of sheath fluid or to focus the core fluid in a well defined region within the channel are significant advantages of the sheath flow device and method.

Figure 11A:
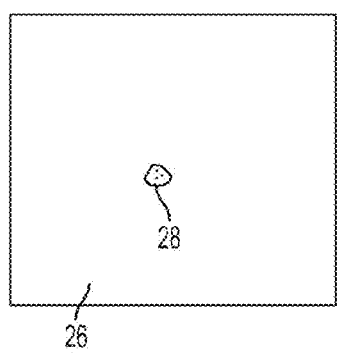
FIGS. 11A-11C are a series of representative cross sections of sheathed flow.
Figure 11B:
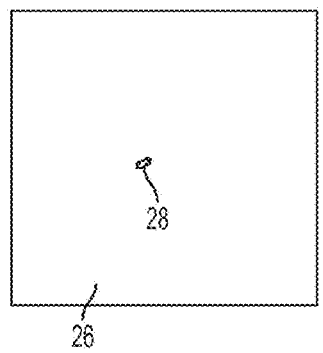
Figure 11C:
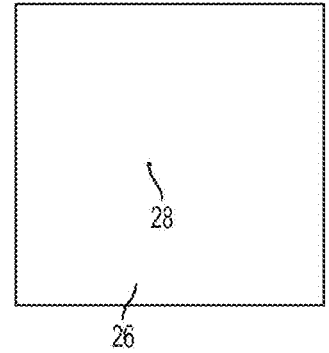

Furthermore, the relative flow rates of the core and sheath can be changed at will and the diameter of the core can be varied in real time if the application warrants, with no need to alter the device itself. As shown in the data in Table 1, the sheathing process remains unperturbed, even at sheath/core ratios over 40,000. FIG. 11a shows a core/sheath ratio of 2,100. FIG. 11b shows a core/sheath ratio of 21,000. FIG. 11c shows a core/sheath ratio of 42,000. Higher resolution microscopes would enable viewing of fluorescence from the core for even smaller core diameters.

TABLE 1

| Reynolds Number | Sheath Flow Rate | Sheath Diameter | Core Flow Rate | Core Diameter Calculated | Core Diameter Measured | Ratio of Core/Sheath |
|---|---|---|---|---|---|---|
| 0.0008 | 21 mL/min | 3 mm | 10 μL/min | 45 microns | 75 microns | 2,100 |
| 0.0008 | 21 mL/min | 3 mm | 1 μL/min | 4.5 microns | 25 microns | 21,000 |
| 0.0016 | 42 mL/min | 3 mm | 1 μL/min | 3 microns | 16 microns | 42,000 |

The actual size of the core can be changed relative to the size of the channel by simply altering the relative flow rates of the core and sheath streams. Furthermore, this change can be effected in real time. Unlike nozzle system traditionally used for flow cytometry or extrusion, there is no need to go to smaller and smaller nozzles which may result in clogging problems, higher back pressures, and reduced output. In previous designs, the core solution must pass through a nozzle or other constriction to enter the flow. This presents a potential clogging point, for the solution containing the cells or other particles to be analyzed. Under the present design, channels can be of uniform size to avoid constrictions and potential clogging points.

Using the device and method described herein, microdialysis could be accomplished without a membrane. The core stream is recaptured after it is exposed by sheathing to the sheath stream. This exposure provides for the removal of low molecular weight molecules by diffusion across the interface of the core stream and the sheath stream. The ability to conduct microdialysis without a membrane prolongs the life of the system. Current microdialysis systems operate for limited lifetimes due to the potential for membrane clogging. Additionally, separations based on differential solubility as well as differential size can be provided by the device and method described herein. For example, a whole blood sample could be sheathed into the center of the channel, and allowed to flow for sufficient distance for small molecules to diffuse outward from the core into the sheath. Cells and larger molecules such as proteins will not diffuse as quickly and will tend to stay in the core. The core would then be unsheathed and recovered, with the smaller molecules removed.

The device and method are useful as a means of protecting conduits, including but not limited to, pipes, tubes, ducts, tubing, capillaries, and microfluidic channels, from fouling or corrosion. A thin sheath stream of protective material is formed around the core stream. The sheath stream need not be the same viscosity as the core stream, therefore a relatively slow moving and thin protective sheath coating can be formed to protect the insides of conduits exposed to corrosive core stream solutions.

The device and methods described herein can also be used to reduce the power requirement for transporting viscous fluids in conduits, including but not limited to, ducts, pipes, tubes, tubing, capillaries, and microfluidic channels. Sheathing a viscous fluid in a second fluid of lower viscosity reduces the sheer stress at the conduit wall which lowers the pressure drop required to generate a given flow rate. The sheath flow component has been used to generate such a flow, in which a core and a sheath stream of differing viscosity initially enter the device side-by-side and the lower viscosity sheath stream sheaths the higher viscosity core stream.

The relatively low flow resistance of the device means that it can be used to sheath quite high-viscosity systems. This is useful in food and polymer extrusion applications. The device and method is further useful in the synthesis of specialty polymeric filaments and tubes. Unlike standard extrusion technologies, filaments with continuously varying diameter can be created. Filaments made in this way can be expected to have increased elasticity over extruded filaments because of the native entropy of the polymer chains. The exact design may also be altered to change the cross-sectional shape of the resulting polymer strand. Since the extrusion device is small, inexpensive, and essentially operates as a passive component, many devices can be fabricated to perform in parallel, such as an array.

The device and methods described are also useful as liquid waveguides. Liquid waveguides have been described for monitoring chemical processes in which light is guided in fluid in a capillary or in the walls of a capillary in order to measure some component of the fluid. The device and method can be used for guiding the light in either the core stream or sheath stream for similar measurements, but with the capability for more exact focusing, much greater control of the relative dimensions of the light guiding fluid and the other fluid, and the avoidance of wall effects such as scattering of the light from the core by the capillary wall. The capability of guiding light in fluids is particularly useful in microfluidic systems.

Figure 12:
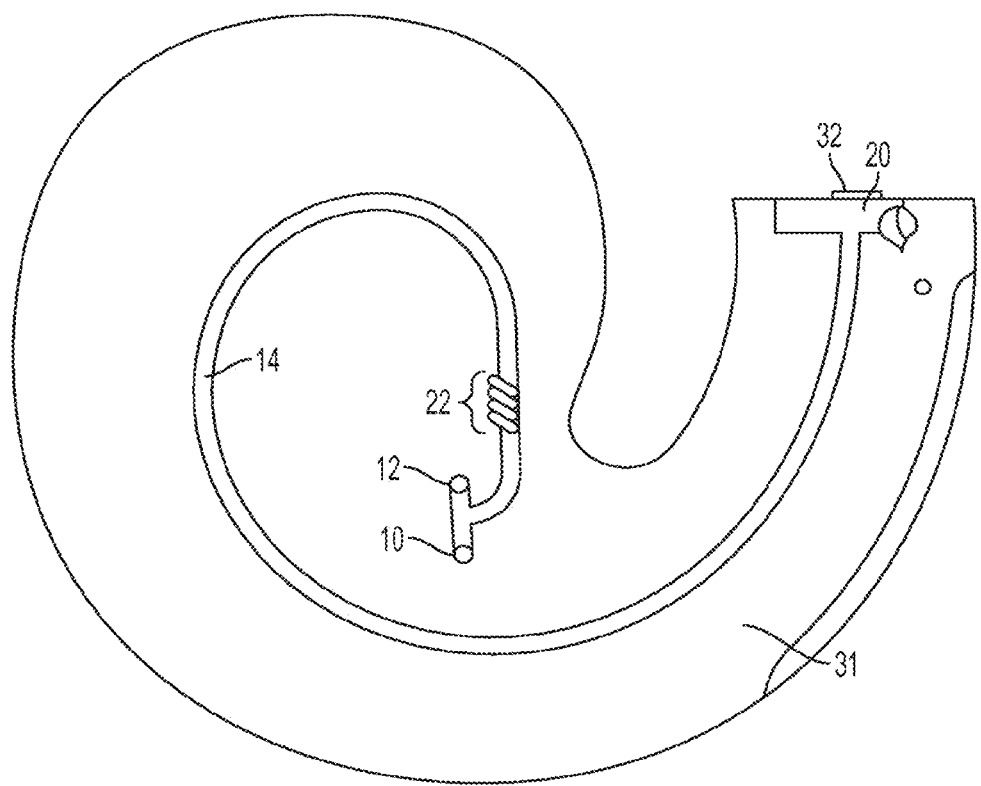
FIG. 12 is a liquid waveguide device.

FIG. 12 shows the waveguide application. A chip 31 was fabricated with a channel 14 beginning in the center and spiraling outward to the outlet 20 on the outside edge of the chip. A sheath stream inlet 10 and a core stream inlet 12, located near the center of the chip, are in fluid connection with the channel 14. The fluid transporting structures 22 sheathe the core stream within the sheath stream. The sheathed solution then travels outward in a spiral of 360 degrees before reaching the outlet 20. A light source 32 is introduced through a window (not shown) located at the outlet 20.

Core and sheath streams are introduced into the structure at the inlets. The core and sheath streams have approximately equivalent densities. The core stream is 70% fructose. The sheath stream is a saturated salt solution with enough fructose added to match the density of the core. There is a small amount of fluorescent dye in the sheath stream. The sheath was formed in the center of the chip 31 and then traveled outward along an increasing spiral.

Figure 13:
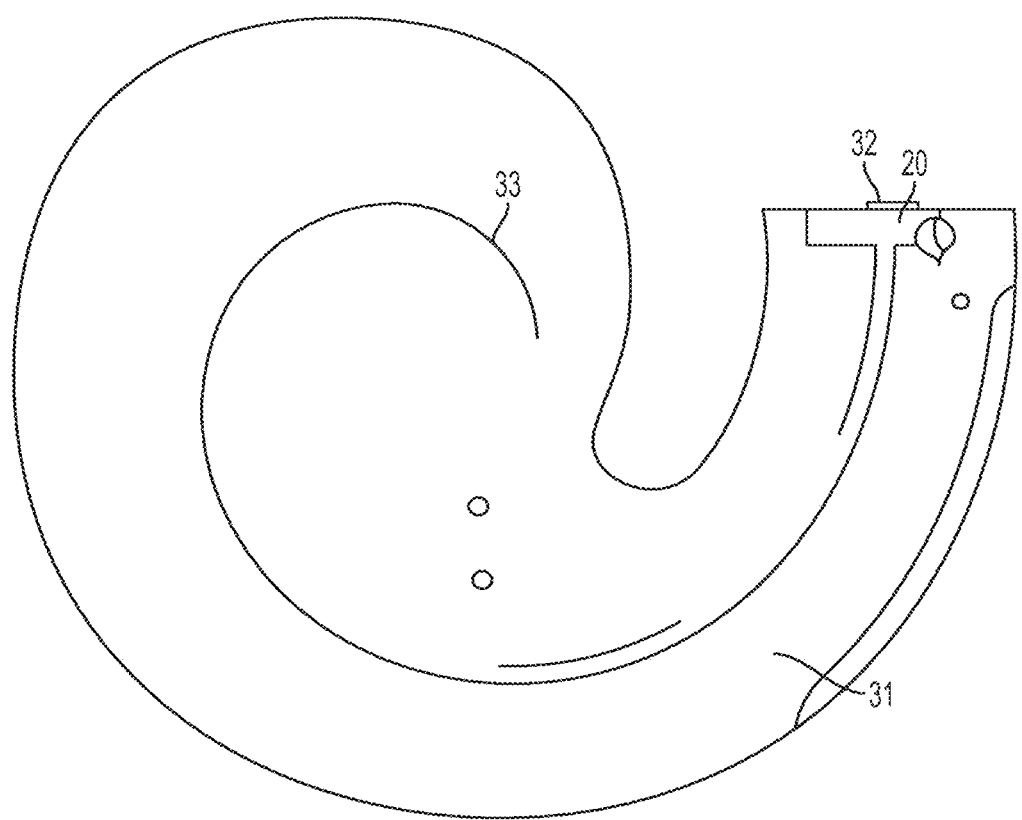
FIG. 13 is a representation of waveguided light though a liquid waveguide.

FIG. 13 shows the resulting waveguided light 33 when light was introduced to the channel from an outlet 20. The light is waveguided 33 through a full 360 degrees around the spiral. The light source 32 illuminates the higher refractive index stream, which in this case is the core; however, it could be either the sheath stream or the core stream.

Figure 14:
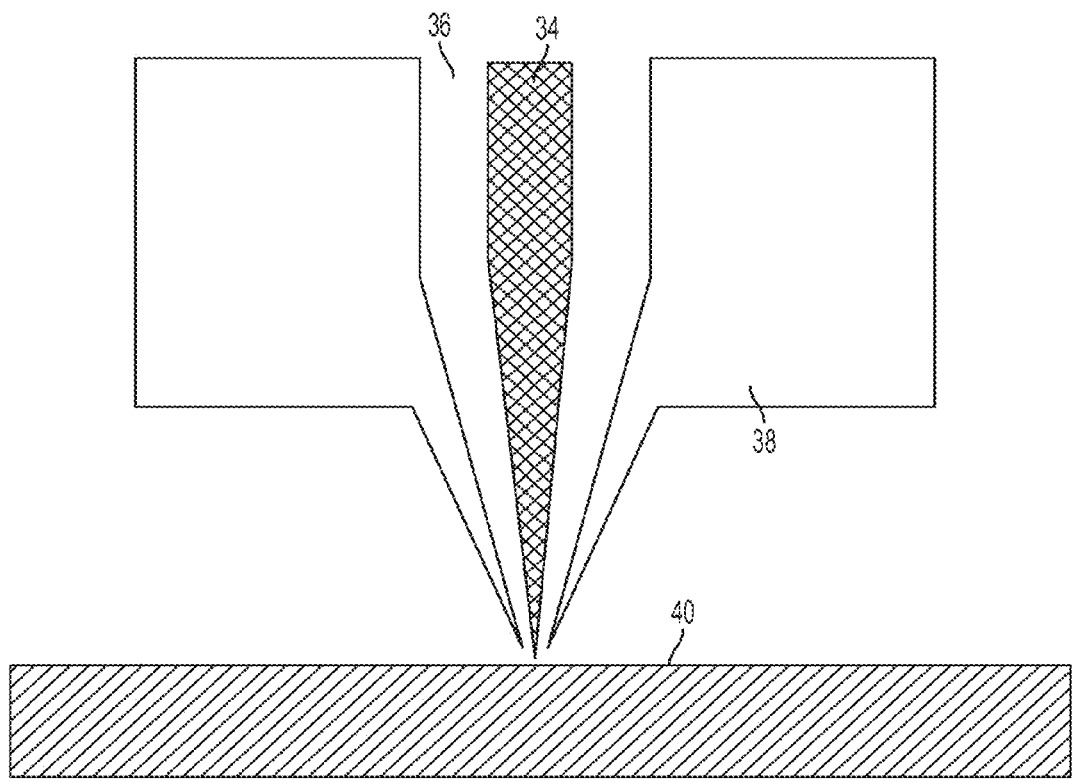
FIG. 14 is a near field microscope.

The condition for waveguiding is merely that the core stream and the sheath stream have different refractive indices. The ability to hydrodynamically focus a core down to submicron diameters allows for the production of a nearfield optical microscope probe entirely out of liquid. FIG. 14 shows an example of a nearfield optical microscope utilizing the present invention. Once the core stream 34 is ensheathed in the sheath stream 36, a tapered nozzle 38 is used to create the taper in the core. The high refractive index core stream 34 is directed through the nozzle 38. Light introduced into the core will be waveguided down to the surface 40. Reflected, scattered, or emitted light will then be collected by the waveguide and carried upward for detection. Another possible design may eliminate the need for a nozzle by introducing dielectrophoretic forces to push the core stream out into a fine tip. This design would also be able to use dielectric forces to steer the stream and raster it over the surface. Based on refractive index measurements of the chosen chemistry, the optimal geometry of the taper can be established. Because a solid tip does not have to be brought into close proximity with the surface, this design is well suited for the analysis of fragile biological samples. It is also well suited to perform liquid-phase photochemistry for nanomachining processes. The chip is able to raster over a surface using a translation stage.

Figure 15:
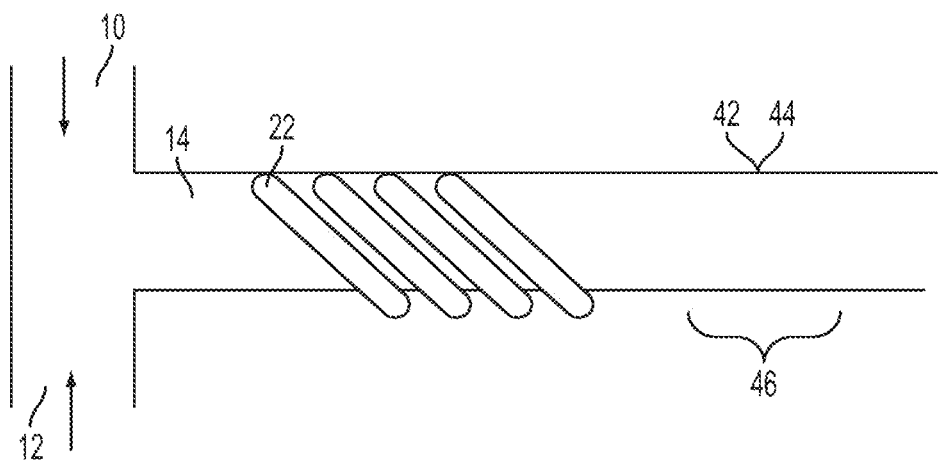
FIG. 15 is a flow cytometer device.

FIG. 15 shows an exemplary flow cytometer using sheath flow. The inlets 10, 12 are connected to the channel 14. The fluid transporting structures 22 wrap the sheath stream around the core stream, focusing the core stream in the interrogation region 46. Interrogation, for example, illumination, comes from a single mode fiber 42. Light was collected by a multimode fiber 44.

Figure 16A:
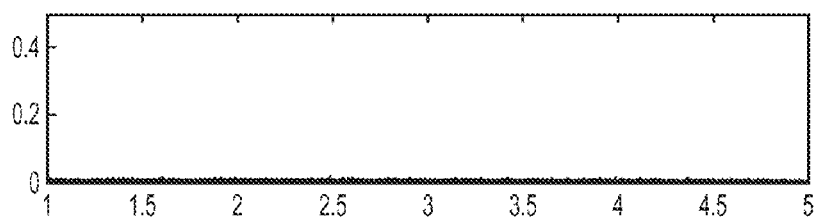
FIGS. 16A through 16E shows the results of tests using the flow cytometer device.
Figure 16B:
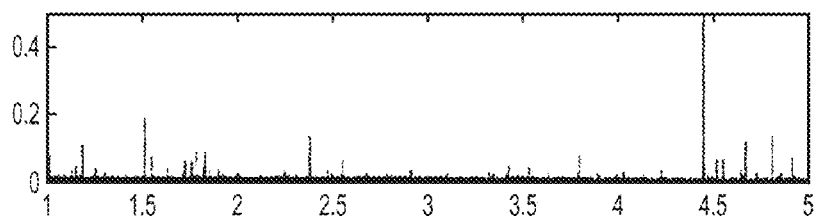
Figure 16C:
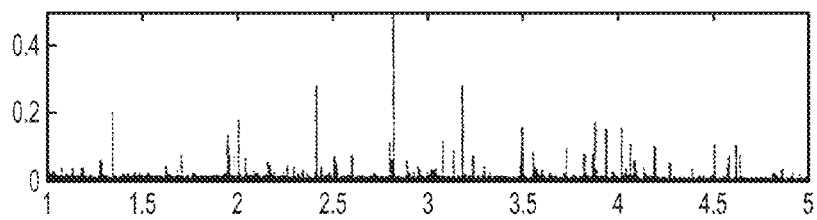
Figure 16D:
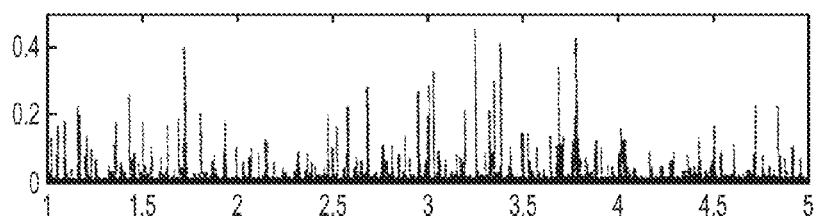
Figure 16E:
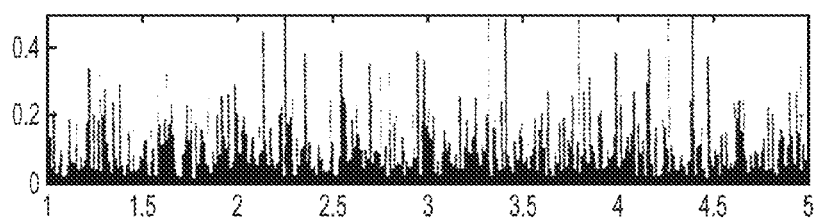

FIGS. 16(a)-16(e) show a series of traces of the light scatter resulting from the series in order of increasing concentration. As shown in the signal tracings, representing the light scatter signal from five-fold serial dilutions of yeast cells, the light scatter signals were proportional to the concentration of cells in the flow stream. The sample core was illuminated with the light from a helium-neon laser introduced via a single mode optical fiber. Scattered light was collected at 90 degrees using a multimode fiber and detected with a photomultiplier tube. FIG. 16a was a highly diluted sample, showing no cells during the 4-second sampling time. Each successive solution was roughly 5 times as concentrated as the previous solution. Each of the spikes seen in a plot represents the passage of a cell through the interrogation region. The number of spikes increases approximately 5-fold with the 5-fold increase in concentration.

The device and method of the present invention are also useful for the fabrication of materials. For example, the core stream can contain a polymerizable, condensable, cross-linkable or crystallizable material, which is extruded to the desired diameter using the sheath stream instead of a solid nozzle or channel. Since the sheath flow device is small, inexpensive, and essentially operates as a passive component, many devices can be fabricated to perform in parallel, such as an array.

Materials from which fibers or other structures can be fabricated include but are not limited to a wide variety of polymers including polystyrene, butyl rubber, polypropylene, polyacrylamide, polysiloxane, and polymethylmethyacrylate. Biological molecules can be ordered to self-assemble into higher order structures; such molecules could include a wide variety of lipids, proteins, carbohydrates and oligonucleotides. Materials that form harder structures could be used including precursors of glassy materials such as sol gels, as discussed in Sousek et al., Polymers for Advanced Technologies, 2005, 16:257-261, incorporated herein in full by reference, or initiators for subsequent deposition of metals, calcium, and/or semiconductors. The fluids used can be aqueous or organic. Preferably, the core and sheath fluid are the same phase.

By varying the diameter of the core, tapered materials can be fabricated. Nonuniform or tapered geometries for waveguides can be generated. Controlling the relative rates of sheath and core flow during polymerization of filaments provides high precision, tapered structures with sub-micrometer diameter fluctuations, resulting in unique waveguiding properties.

The device and method is further useful in the synthesis of specialty polymeric filaments and tubes. Unlike standard extrusion technologies, filaments with continuously varying diameter can be created. Filaments made in this way can be expected to have increased elasticity over extruded filaments because of the native entropy of the polymer chains. The exact design may also be altered to change the cross-sectional shape of the resulting polymer strand.

By configuring the grooves or ridges used to transport the sheath stream, non-round shapes can also be obtained. In addition to varying the rate of flow to change the diameter of the core, the core fluid can be pulsed instead of flowed continually to stop and start the core stream to form "particles" or "packets" of core fluid. Once the desired size and shape are obtained, the material in the core is polymerized, condensed, cross-linked, or crystallized chemically, optically or by other means known in the art. Due to the geometry of the system, this type of synthesis can be conducted in continuous manner rather than in batches. Moreover, the geometry of the system is particularly amenable to the production of high-aspect-ratio structures and filaments that are especially difficult to produce in quantity.

Shapes that can be fabricated in this method include, but are not limited to, ovals, ribbons, rods, wires, tubes and filaments. Using the grooves or ridges on the top and bottom of the channel can be specifically designed to produce the desired shape. The grooves or ridges do not have to be straight but can have a variety of configurations as long as they channel the fluid around the core. They can be curved, in the shape of chevrons, angled like "check marks," or in a variety of other shapes in order to influence the shape of the resultant core fluid. The addition of more inputs and grooves further downstream can be used to expand the repertoire of shapes that can be fabricated.

More complex shapes that can be designed and fabricated using grooves or ridges include hollow cylinders, filled "sausages," coated particles, rods with alternating composition, also known as "nano bar codes". Structures with longitudinal or lateral density or chemical gradients can be fabricated by introducing gradients into one of the flow streams (longitudinal) or by allowing a reactant to diffuse in or out of the core while it is in contact with the sheath stream (lateral).

Figure 17:
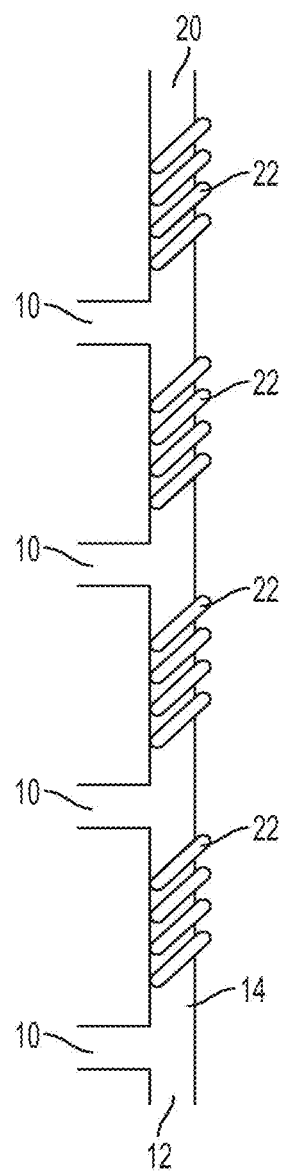
FIG. 17 is a view of one example of a sheath flow device.
Figure 18:
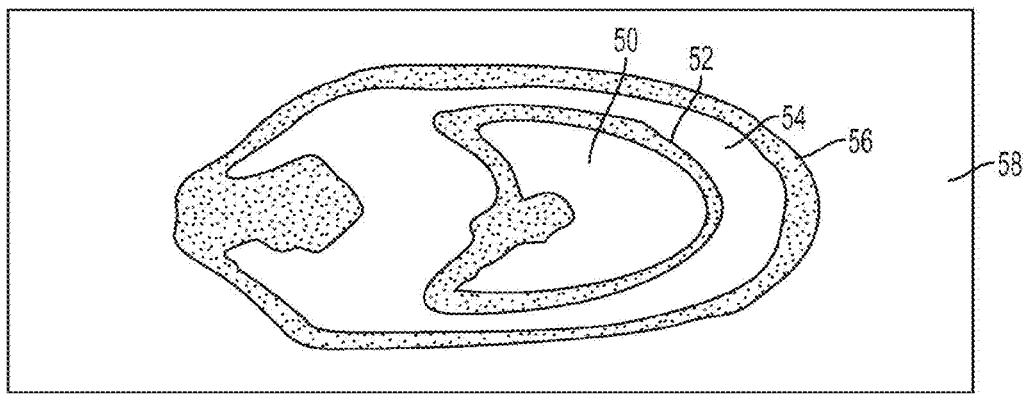
FIG. 18 is a tube within a tube made by the sheath flow device.

FIG. 17 shows a sheath flow device capable of creating a hollow tubes within a hollow tube. A sheath input 10 and a core input 14 are connected to a channel 14 having a series of fluid transporting structures 22. A series of successive sheath inputs 10 are provided downstream towards the outlet 20. Each successive sheath input 10 creates a new sheath around all the previously sheathed materials. FIG. 18 shows a hollow tube within a hollow tube that was made by using the device of FIG. 17 by alternately introducing input streams and ensheathing the structures. The deepest interior core stream 50 is surrounded by successive core/sheath streams 52, 54, 56, followed by sheath 58. Streams 52 and 56 were labeled with a fluorescent dye for contrast.

Typically, the sheath stream is sufficient to move the polymerized material to the output of the channel. For some materials, however, as the extruded material polymerizes and its viscosity increases from its unpolymerized value to infinity, the dynamics of the flow profile within the channel may change to the point that feed matching is required to control the fluid velocity and effectively remove the polymerized material. There are several options available to do feed-matching. In an elastomeric chip, the fluid velocity is controlled by compressing the channel to cause the fluid to accelerate. Additionally, rollers may be placed at the exit of the chip so that they impinge on the rod and control the linear exit velocity of the polymerized rod.

Generally, the core contains a polymerizable material and is extruded to the desired diameter using the sheath stream instead of a solid nozzle or channel. Once the desired shape is obtained, the core material is polymerized chemically or optically. Due to the geometry of the system, production can be in continuous instead of in batch mode. Moreover, the geometry of the system is particularly amenable to the production of high aspect ratio structures and filaments which are especially difficult to produce in quantity. Since the fabrication device is small, inexpensive, and essentially operates as a passive component, many devices can be fabricated to perform in parallel, such as an array.

Multiple Fibers Fabricated in a Single Channel.

Figure 20:
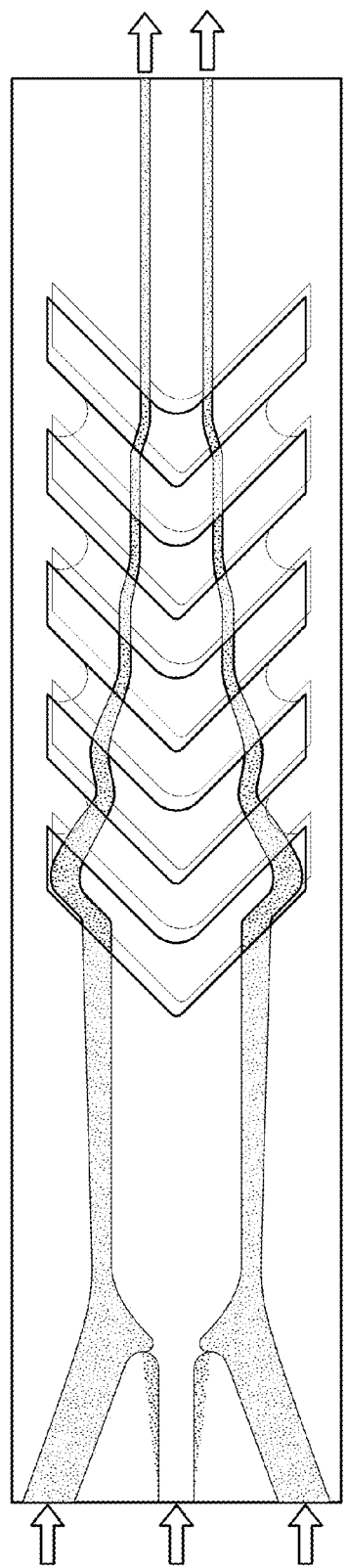
FIG. 20 shows how parallel core streams may be used for simultaneous shaping of two core streams. Polymerizable material is input from two outer (left) sides of the main channel and the sheath fluid is input into the center of the main channel. The grooves channel the polymerizable material and sheath solution so that the prepolymer flows remain separate, but are completely surrounded with sheath fluid. Following polymerization, the result will be two parallel shaped fibers exiting from the same channel.
Figure 21A:
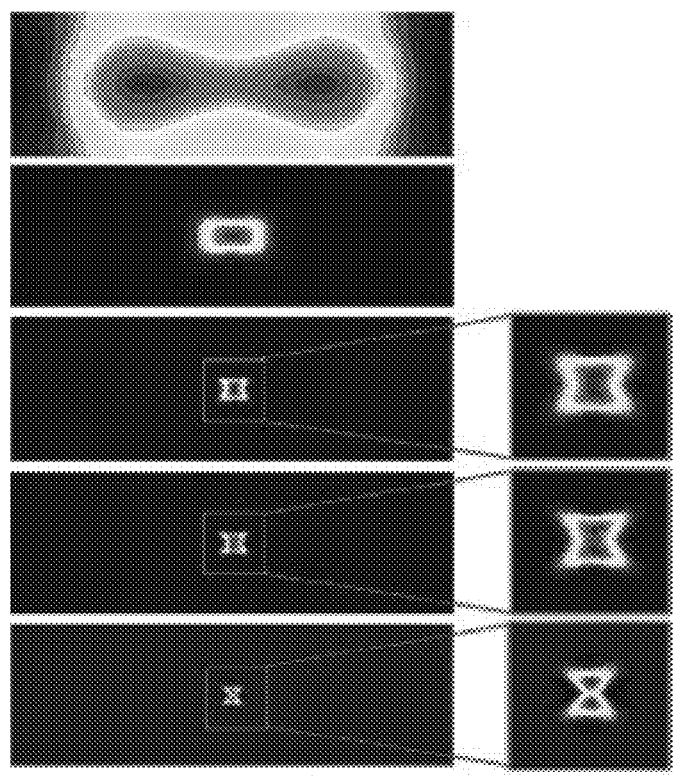
FIGS. 21A and 21B show how a split core may be obtained by controlling the relative flow rates of the core and sheath. A single stream of polymerizable material can be split into multiple streams using the appropriate combination of wall structures and relative flow rates. The simulation of FIG. 21A shows a channel with 7 chevrons in the top and bottom and prepolymer and sheath flow through the channel at flow-rate ratios of (a) 1:1, (b) 50:1, (c) 500:1, (d) 1000:1, and (e) 2500:1.
Figure 21B:
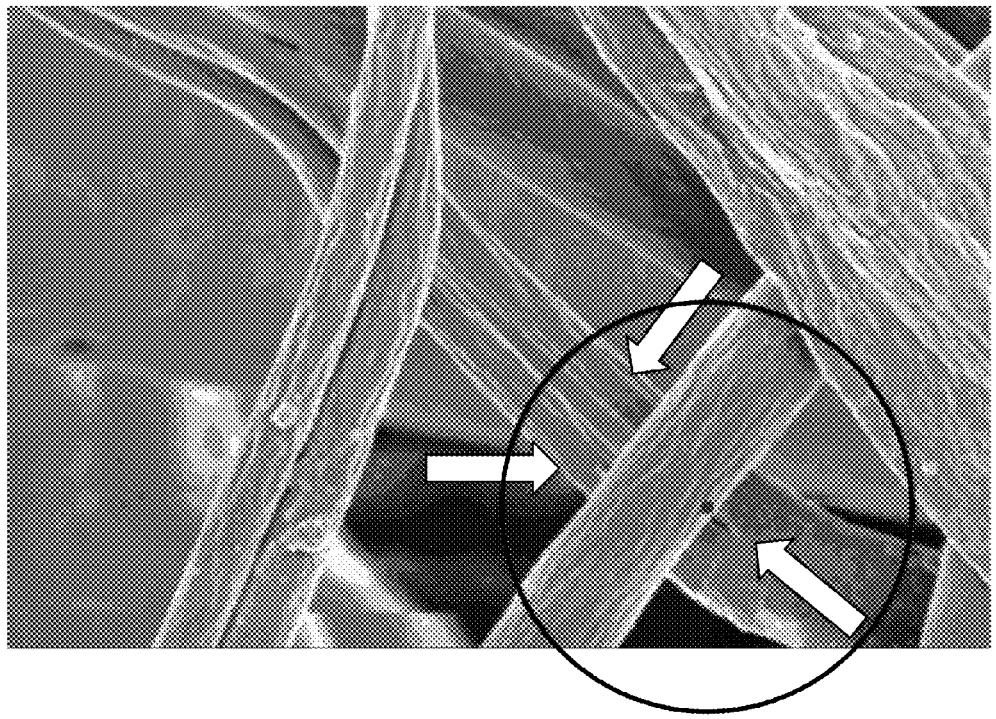
Figure 22A:
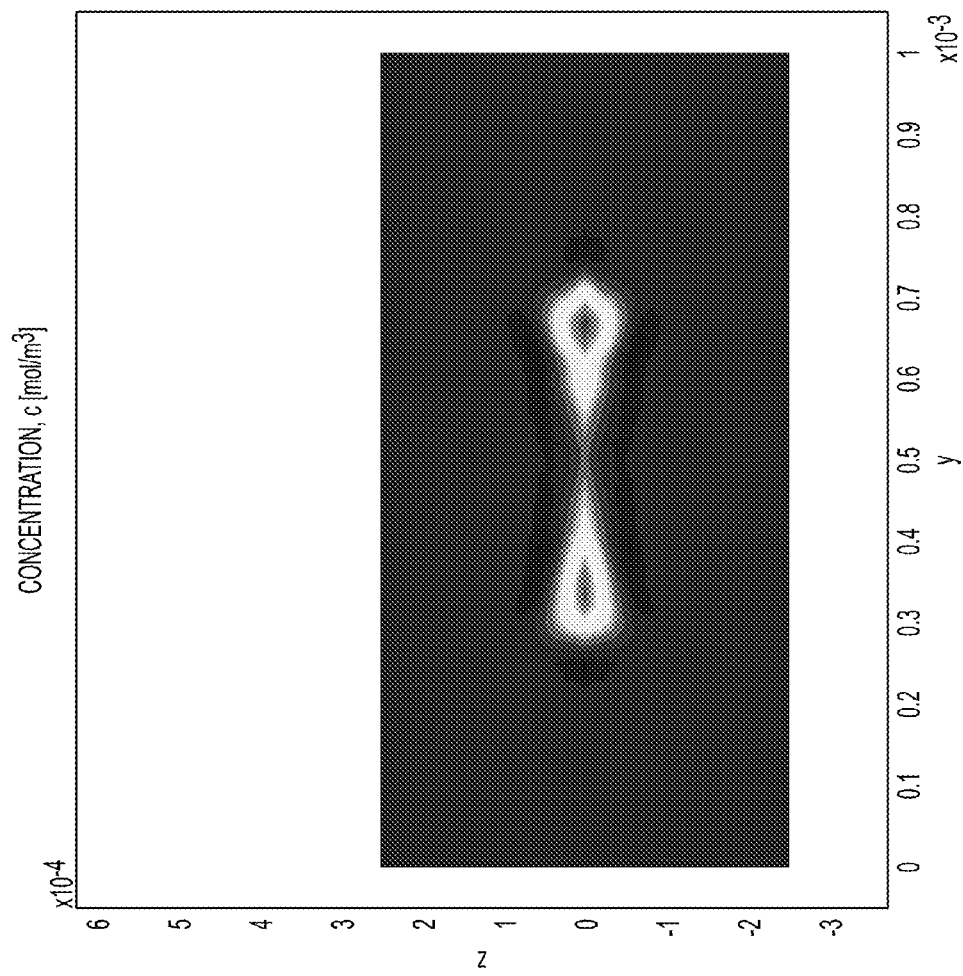
FIGS. 22A and 22B shows a simulation of how flow through a 5-chevron device can be used to split a single core into two parallel streams.
Figure 22B:
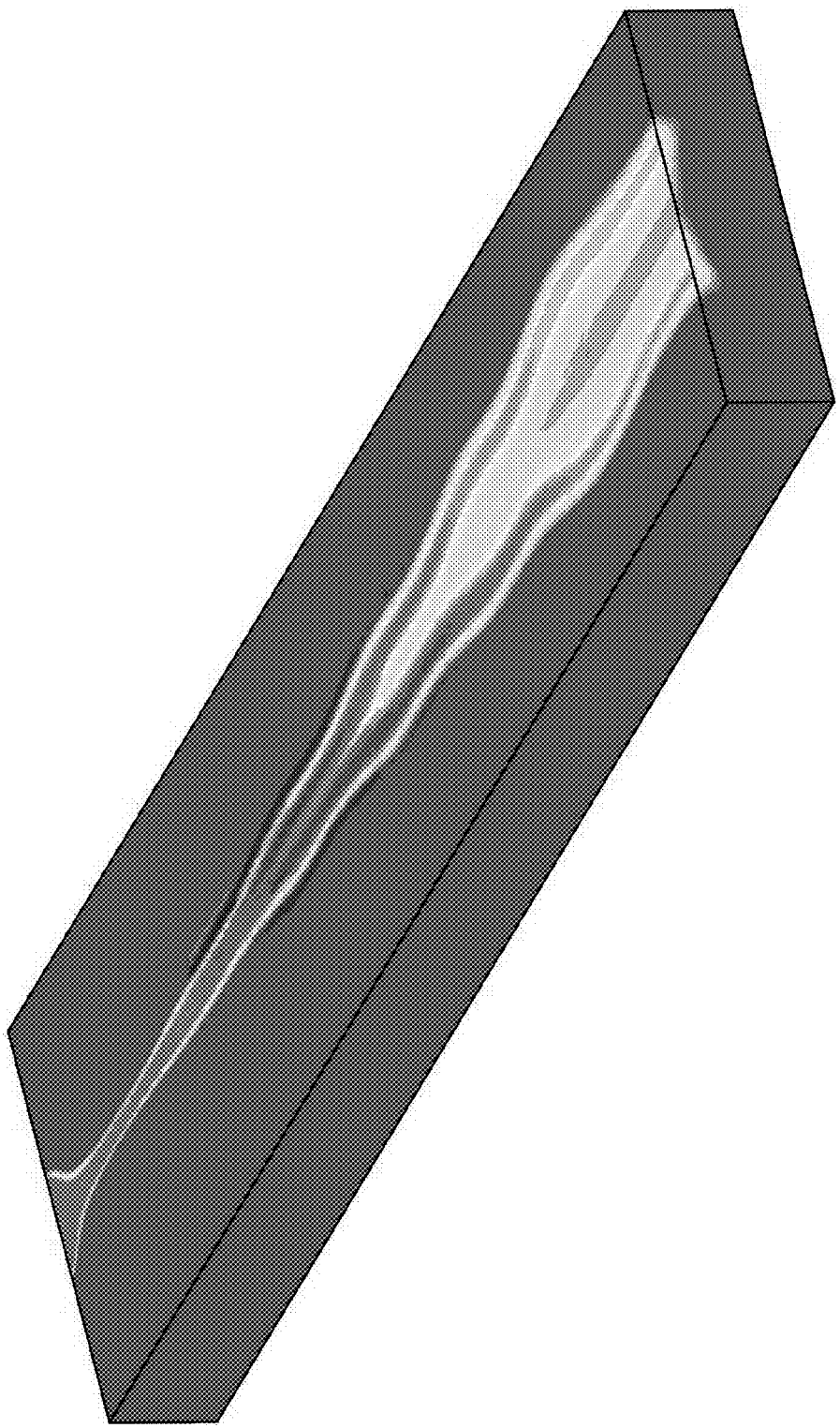
Figure 23:
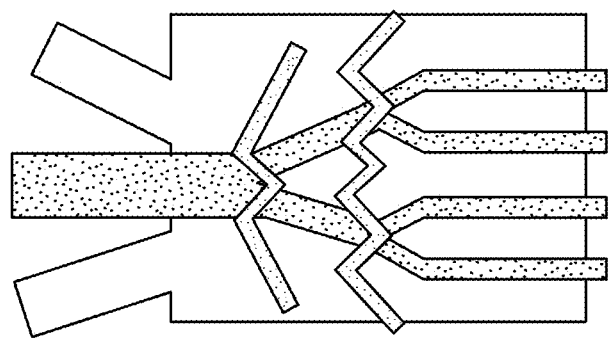
FIG. 23 shows how structures in a channel can be used to split a single core stream (black, input to center of a channel) into multiple streams for production of multiple parallel fibers.

Structures, including but not limited to grooves, ridges, and pillars, can be made in the channel floor and roof such that multiple fibers can be produced in a single channel configured to produced multiple sheathed flows. The core streams in the multiple sheathed flows are polymerized to form multiple fibers therefrom. This can be accomplished by shaping multiple inputs of polymerizable material as in FIG. 20 or by splitting a single prepolymer stream into parallel streams as in FIGS. 21A and 21B, which show a simulation and actual splitting, respectively, of a fiber caused by controlling both grooves in the top and bottom of the channel and the relative flow rates of the sheath and polymerizable material. By changing the flow-rate ratios, fibers could be fabricated with split regions that recombine into a single fiber. This could be done repeatedly to obtain individual fibers with repeated split regions. FIG. 23 exemplifies a top-down view of a design that could be used to create multiple parallel fibers.

In embodiments, a split fiber has two lobes that remain attached, or the split may be complete so that two or more distinct fibers arise, such as from a corresponding number of distinct core streams.

Production of Fibers with Dimensions Altered Along Length of Fiber.

Figure 24:
FIG. 24 shows a fiber with variable dimensions. The fiber was cast from acrylate in a grooved fluidic channel with variable pump pressure on the inlets to alter the flow-rate ratio of core and sheath streams.

Relative flow rates of the polymerizable material(s) and sheath solution(s) can be altered during the polymerization/casting process to create fibers with variable dimensions along the length of the fiber. In FIG. 24, variations in the pump speed changed the ratio of flow rates of polymerizable material and sheath to produce a fiber with a cross-section that alternately thickened and thinned. The ability to taper a fiber could be especially useful for optical applications.

Production of Particles, Rods and Packets.

Modifications in the methodology for producing shaped fibers can be used to produce particles, rods, or packets in the same type of microfluidic devices. A packet refers to an enclosed hollow shape. The method of use can generate control over the length of the structures by a variety of mechanisms while the cross-sectional shape is determined as already described for fibers. Mechanisms for breaking the continuity of the core stream can include "chopping" the light used for UV polymerization to make rods or particles with defined length; subjecting the core to piezoelectric, acoustic, or other alternating forces to move the core back and forth in the sheath stream; alternating polymerizable and nonpolymerizable chemical solutions in the core stream; and/or using variations in flow-rate ratios to pinch off the core into discrete parcels.

Similarly, magnetic or electric forces could be applied in a fixed or modulating fashion across a channel in order to modify the alignment of material, including the polymerizable material and/or content suspended therein. Such forces can also be used to create a gradient, discussed below.

Electric or magnetic fields can also be applied longitudinally along the channel (parallel to the direction of flow) to encourage alignment of polymer chains. For example, with cationic polymerization, a longitudinal electric field could draw the positively-charged reaction centers in a direction along the forming fiber, causing the polymer backbone to trail behind.

Production of Fibers with Encapsulated Cells, Enzymes or Other Biological Elements.

Fibers or packets could be made with biocompatible polymers, including but not limited to collagen, agarose, polyelectrolytes, chitosan, gelatin, polyethylene glycol, or peptides, and derivatives of these molecules, and used as matrices, scaffolds or hollow supports for tissue engineering or extended cell culture for cells from mammals or other animals. Hollow fibers or packets could include cells (such as mammalian cells), the cells could grow on inner or outer surfaces of the fibers with nutrients and/or antibiotics delivered through the fibers, or cells could be embedded in the fibers. A significant advantage of this technique is that the cells can be introduced during the manufacture of the fibers, in the lumen, in a biocompatible prepolymer layer, or in the surrounding sheath fluid. Alternately, a conventional approach of making the scaffold structure and introducing the cells thereafter is also possible. The applications for such materials include, but are not limited to, medical and scientific research, wound healing, tissue engineering, pharmaceutical screening, and bioprocessing.

Fibers could be used to encapsulate cells (such as bacterial cells) or spores selected or engineered for biomanufacturing, biosensing, or bioremediation. For use in the field, whether as sensors or for decontamination, cells must simultaneously be protected from the environment and exposed to it. The level of tolerance to non-optimal conditions is much higher for bacteria genetically modified for sensing or selected for degradation capability than for animal cells, though the latter are also under development. Bacteria have been encapsulated, immobilized, or used free in solution. The first approach usually stabilizes the bacteria but can limit transport of the target compound to the bacteria, the second often damages the bacteria, and the third requires large quantities relative to the fluid being tested. Testing times range from hours to days, depending on the resistance of the bacteria to the toxicity of the sample matrix.

The inclusion of target-reactive bacteria in hollow fibers, along with nutrients and stabilizers (e.g. trehalose), can be used for continuous monitoring of effluents from air samplers, drinking water, or other sources. Cell lines reported in Anal. Chem., 82: 6093-6103 (2010) are exemplary candidates for such use. These cells form spores that are highly stable for long periods (24 months at room temperature or 12 months under extreme temperature and humidity/drought environments), yet can be germinated and produce a measureable response to target analytes in ~2 hours. The two genetically modified lines generate a luminescent signal in the presence of zinc (*Bacillus megaterium*) or arsenic (*Bacillus subtilis*). The zinc sensing system employs the enhanced green fluorescent protein (EGFP) as a reporter, which is detected by exciting with UV light, while the arsenic sensing system utilizes β-galactosidase, which can be detected by a chemiluminescent substrate. Substrates are present within the spores and do not need to be added exogenously. Spores are ideal biosensing elements in that they are rugged, inexpensive to produce and easy to make and germinate. Indeed, sensing spores can be cycled from dormant to active over a period of at least two years without any significant loss in their analytical performance. Moreover, storage of spores under a variety of stressful and stringent conditions does not affect their sensing ability when brought back to active cells.

Since the conditions for shaping the fibers with hydrodynamic focusing are typically performed with relatively low sheer stress and the polymerization conditions are generally mild (casting or brief exposure to UV light), the fibers can be formed with cells present in one of more of the fluids. For incorporation of cells into the polymer layer, the cell-containing fluid, including stabilizers if necessary, and hydrogel, protein, and/or other prepolymer (preferably biocompatible) is focused with a sheath solution that is also preferably biocompatible and of matching viscosity. Microchannels with grooved structures in the top and bottom of the channel can be designed to use a phase-matched sheath fluid and were demonstrated to focus a polymerizable core stream into a predetermined shape without mixing. The cross-sectional dimensions can be determined by the relative flow rates of the sheath and core. Using multiple fluid additions, successive layers of fluids can be wrapped around the core. The cell-containing core fluid, including stabilizers if necessary, and a hydrogel or other biocompatible polymer is defined so that it matches the viscosity of the fiber prepolymer. The composition of the fiber prepolymer is designed for rapid polymerization without cell damage; in addition to the acrylate recipes used to date, we can use polymers based on click chemistry (e.g. Applications of click chemistry themed issue of Chemical Society Review, edited by M. G. Finna and V. Fokin 2010, especially C E Hoyle, A B Lowe, and C N Bowman Chem. Soc. Rev, 2010, 39:1355-1387). Composition and thickness of the hollow fiber layers can be adjusted as necessary to provide strength and stability with maximum diffusive transport.

In experiments designed to demonstrate fabrication with cells, bacteria were included in a hydrogel prepolymer and bio-hybrid fibers were fabricated using hydrodynamic focusing as described in Daniele M A, North S H, Naciri J, Howell P B, Foulger S H, Ligler F S, et al. "Rapid and continuous hydrodynamically controlled fabrication of biohybrid microfibers," *Advanced Functional Materials.* 2012, 23:6 698-704. The cells were viable after the polymerization of the fiber and capable of continued proliferation in the fiber.

Figure 30:
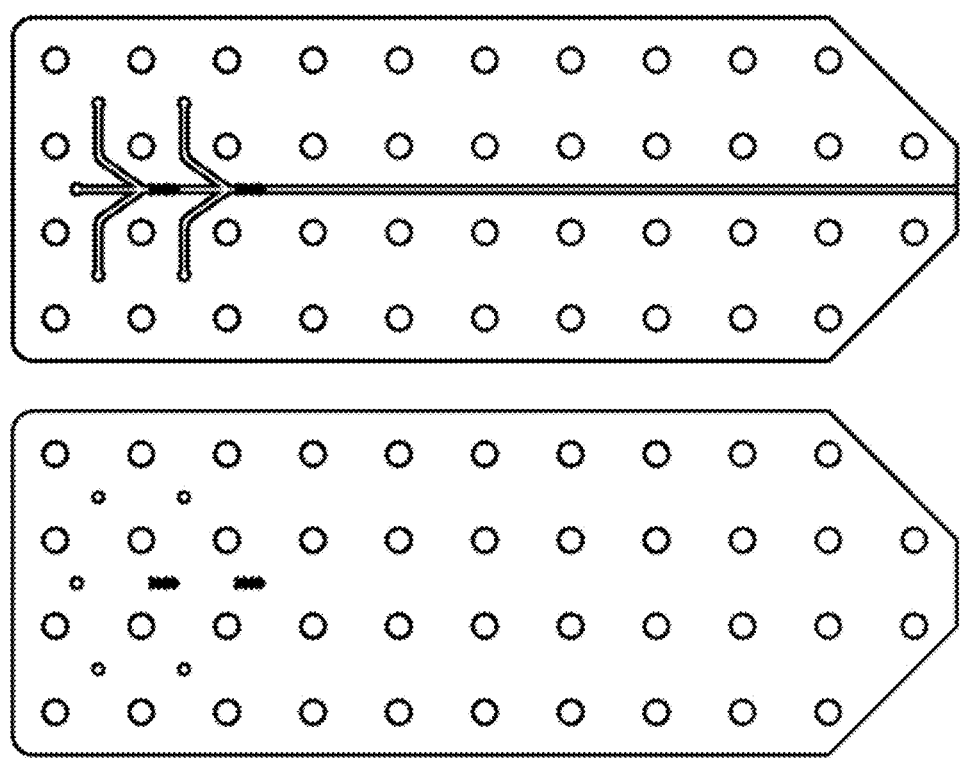
FIG. 30 schematically illustrates the cover and substrate layers of a sheath flow device used to manufacture hollow (or multi-layer/component) polymer fibers.

In another experiment, hollow fibers were made using hydrodynamic focusing. FIG. 30 shows a device that focused first a nonpolymerizable core fluid with a polymerizable sheath fluid (introduced from a single reservoir into inlets on both sides of the core inlet). From left-to-right, a core fluid is introduced and hydrodynamically focused vertically in the center of the channel by the first sheath fluid. The fluids traverse the chevrons that serve to: (1) compress the core fluid vertically and (2) symmetrically wrap the sheath fluid about the compressed core. This concentric two-component flow stream then encounters a second sheath fluid, whereby it is focused again hydrodynamically in the vertical direction while being encircled in the second sheath fluid after traversing the second set of chevrons. The microfluidic channel that follows serves as a reactor where photoinitiated polymerization is carried out, locking in the shape of the polymer. The core fluid and first sheath fluid can be independently polymerizable materials yielding either a two-layer/component solid fiber or a two-layer/component liquid core solid shell fiber which is equivalent to a hollow fiber. Also, it is important to note that the final sheath used to protect the concentric flows from contact with the microchannel walls can be doped with reactive species complementary to the chemistry used in the outermost shell or in the lumen to form additional thin polymer layers that correspond to the diffusion boundary of the photoinitiator containing outer shell. This approach might serve to add a skin-like layer to enhance integrity or mimic the membranes around (for example) muscle fibers. Such an embodiment is also described below under "Production of fibers via interfacial reactions."

Figure 31:
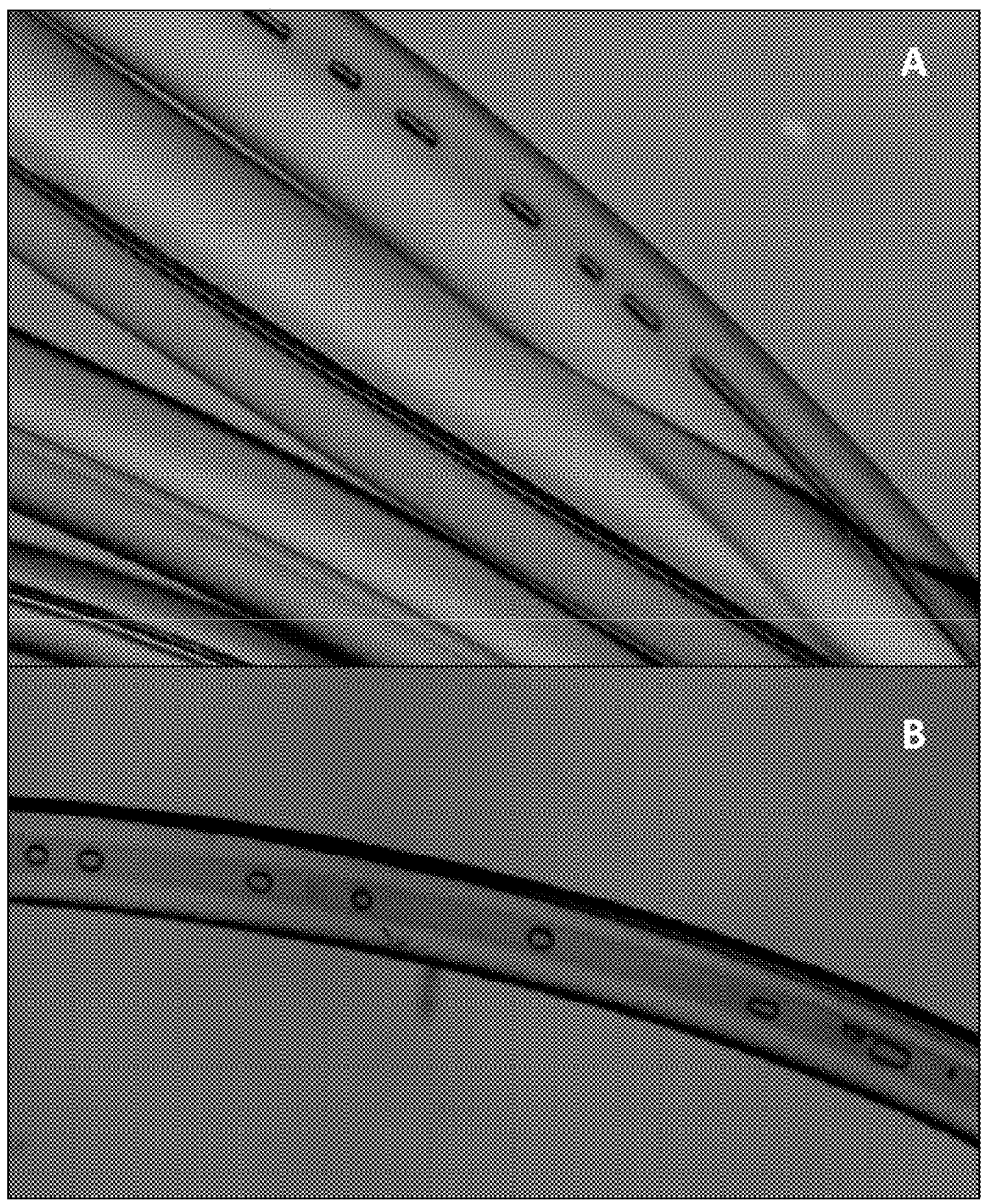
FIGS. 31A and 31B show hollow PEG fibers manufactured using the device shown in FIG. 30.

In a second shaping region, the first set of core and sheath streams essentially travelled down the channel as the core fluid and were ensheathed with a nonpolymerizable fluid of equivalent viscosity. In this experiment, hollow fibers or tubes were produced, as shown in FIGS. 31A and 31B, with air bubbles passing through the lumen for easier visualization of the inside of the hollow fiber. Hollow microtubes were produced with diameters on the scale of arterioles and venules, i.e. "capillary-sized" fibers.

A cell-fiber system incorporating bacteria is preferably designed to accomplish the following:

1. The cells are stabilized in a ready-to-use format during shipping and storage at room temperature.
2. Nutrients needed for cell reactivation are encapsulated into the cell-fiber mat for operator convenience using several strategies.
3. The cell-fiber mats provide high surface area-to-volume for sample interrogation.
4. The cell-fiber mats provide a convenient footprint for automated, continuous monitoring.
5. Optics for luminescence detection are very simple (filter and photodiode) and can be battery operated.
6. Cells with new specificities for detection, catalysis or degradation can be genetically engineered and incorporated into the fibers, either singly or in mixtures.
7. The fiber mats prevent release of genetically modified organisms into the environment. Used materials can be easily destroyed for safe disposal.

The technology developed for sensing can be extended to decontamination with the availability of appropriate cells. The fibers can be aligned or woven to make filters for decontamination or textiles for protection of warfighters or hazmat workers.

Fibers or Particles with Encapsulated Enzymes or Other Biological Elements.

The embedding of active biomolecules (such as enzymes or other proteins) in the fiber is simpler than encapsulating active cells. Methods for encapsulating active enzymes in hydrogels, sol gels, polymer beads, polyanionic films, and other materials are well documented. Nevertheless, there is still a need for maintaining biomolecular activity in filters, woven fabrics, beads, and other solid phases used for biomanufacturing, separations, remediation, protection, and sensing. The active biomolecules can be encapsulated randomly throughout the shaped fibers, along with any required stabilizers or cofactors, or these molecules can be included in a core layer surrounded by a layer polymerized to have the optimum porosity for the desired function. Molecules that promote capture and transport of the target from the outside to the inside of the fiber can be included throughout or just in the outer layer(s).

For example, the fibers could include a polymer matrix of appropriate porosity and containing carboxylic moieties, $Cu^{2+}$ chelated to the vinyl groups for binding phosphonates, and an enzyme for catalysis. It has been demonstrated that hydrodynamic focusing in microfluidic channels can be used to fabricate porous acrylate fibers with pre-designed cross-sectional shapes (see Thangawng et al., *Lab Chip* 9 (2009) 3126-3130). Round fibers or flat ribbons have been made with dimensions from ~300 nm to ~300 µm in lengths up to meters. The fibers have been spooled so that they are aligned in parallel or collected them in randomly organized mats. The fibers have been characterized in terms of shape, dimensions, molecular organization, and tensile strength. Depending on the size and method of polymerization (casting or UV), the fibers can make them more or less porous. A key metric will be the amount of liquid or air that can be wicked into a gram of fiber, which will depend on the fiber geometry, weave pattern (pores, capillary action), and fiber chemistry (surface wetting, swelling, internal porosity). Shape and organization are important since as the distance that the toxic agent must diffuse from the surface of the fiber to the active components is decreased, the faster the target molecule can be bound and/or degraded.

The same considerations apply to the encapsulation of molecular recognition elements, with or without enzymatic activity. Once could design fibers or particles that include sensing molecules along with molecular elements for signal generation, including but not limited to fluorescence, chemiluminescence or electrochemical signals. The response to molecular recognition could include controlled release of a drug or therapeutic, such as the release of insulin in response to detection of high glucose levels in vivo.

Shaping of Fibers for Assembly into Larger Scale Materials with New or Improved Properties.

Round or non-round fibers may be formed into larger scale materials. Exemplary larger scale materials include, for example, textiles, composite films, environmentally sensitive smart materials, high strength materials, cables, yarns, etc. Fibers produced by standard methods such as extrusion or electrospinning are round due to the minimization of interfacial tension at the boundary between the prepolymer core and surrounding air or other phase, however the properties of non-round fibers may be exploited in larger scale materials. For instance, post-polymerization modification, such as twisting, of non-round fibers can create periodic structures in the fiber. Larger scale materials can also be prepared by techniques known to those of skill in the art, for example, spinning, weaving, and/or nonwoven production methods (staple nonwovens, spunlaid nonwovens).

Figure 25:
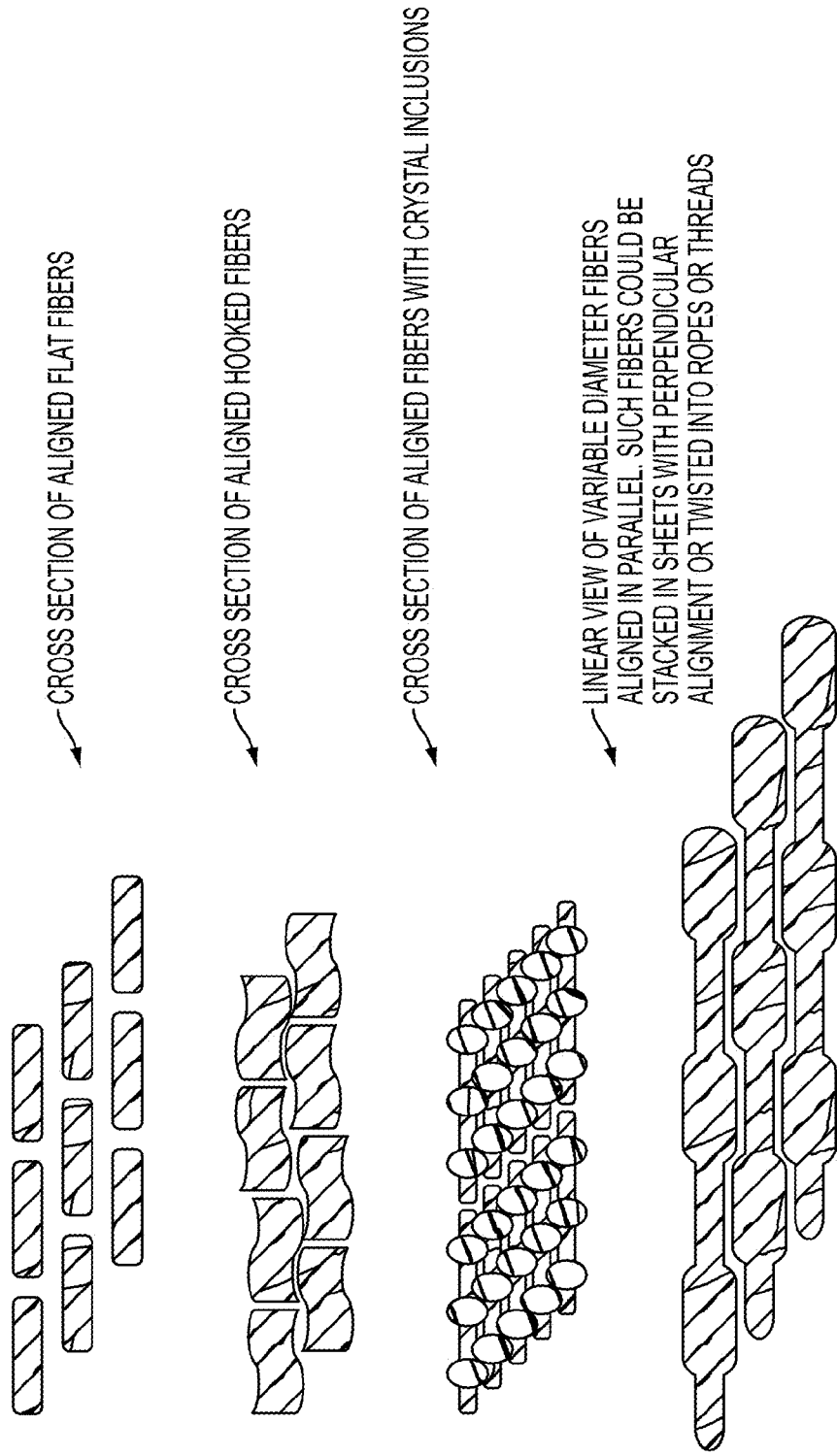
FIG. 25 shows examples of organizing shaped fibers.
Figure 26A:
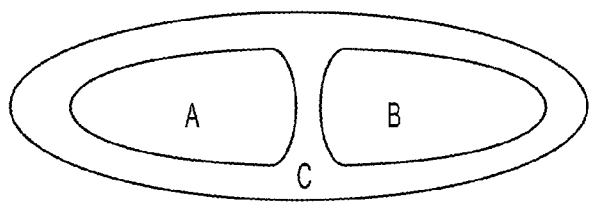
FIG. 26A shows example of multi-component fiber cross sections.
Figure 26A:
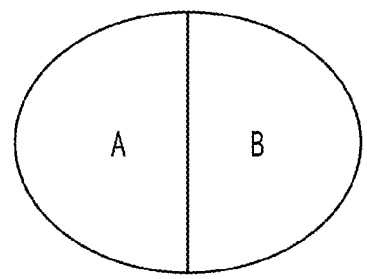
Figure 26A:
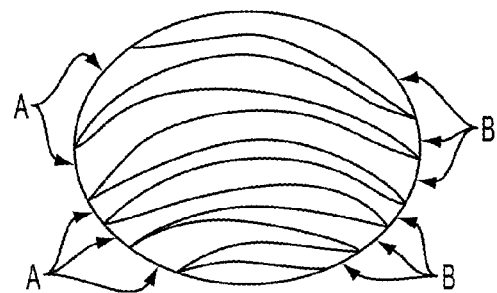
Figure 26A:
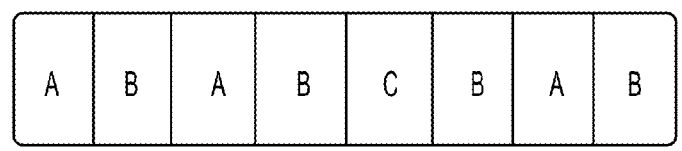
Figure 26B:
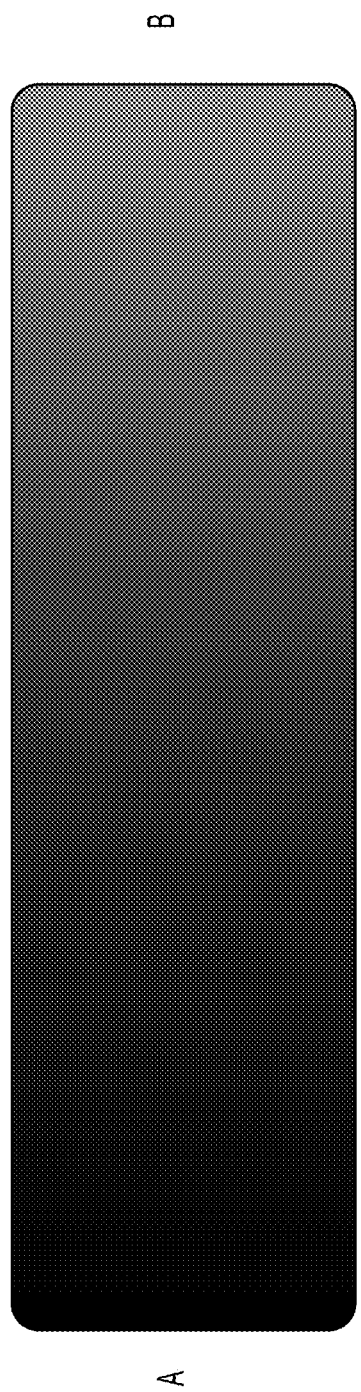
FIG. 26B shows a schematic cross-section of a fiber with a gradient cross-section.

The interaction of shaped filaments or fibers in such materials could provide new or improved strength, flexibility, potential for actuation, or other new properties. For example, alignment of many small filaments within a rope or textile leads to improved strength compared to individual large fibers. Various types of fiber shapes and exemplary larger scale materials are illustrated in FIG. 25.

Phase-separating materials, such as certain polymer blends or block copolymers can be used to cause the self-assembly of structures within or on the surface of the fibers. These structures may be aligned with or across the fiber and can play a role in the formation of larger scale materials.

Production of Fibers Via Interfacial Reactions.

The polymerization, precipitation, or other hardening reactions can be initiated by the combination of compounds that takes place at the core/sheath boundary, or other interface between streams such as between an interior core stream and exterior core stream. It is also possible to have multiple streams that come in contact to produce a reaction. Such technology could be broadly classified as an interfacial reaction.

The kinds of interfacial reactions that can produce polymers during hydrodynamic focusing can generally be classed into two categories. In the first, the reaction that takes place at the interface immediately produces a solid product, which ultimately seals the interface and caps the reaction so that the reaction is limited to the interface. The result would be an extruded material at least initially in the shape of the interface. One example of such a reaction is in the production of nylon, such as at a hexane/water boundary. The second category of reaction is one which can continue to propagate into the bulk of the material once the two flows are brought into contact, for example precipitation of PMMA described below, wherein the PMMA solvent is still mobile in the solidified PMMA, and continues to leave the fiber even after the perimeter has already hardened. Another example would be the introduction of an initiator to a living polymerization. Once initiated at the interface, the reaction center can then continue to migrate into the bulk of the liquid monomer.

In an example of an interfacial reaction propagating into the bulk of the material, a solution of polymethylmethacrylate (PMMA) in acetone (other suitable solvents can be used) was sheathed in an aqueous solution. As solvent diffused out of the core into the sheath, the PMMA precipitated to form a fiber. In addition to simple precipitation, other reactions can be used, including acid/base chemistry, introduction of chemical initiators, and step-growth polymerization.

Although the shaping grooves function most reliably in one-phase systems, fibers have been produced in two-phase systems as well. It is also possible to temporarily remove the interface of a 2-phase system by placing a thin layer of an intermediate solvent between the two materials. As an example, a thin layer of isopropanol (IPA) can be placed between water and hexane. Being miscible with both water and hexane, the IPA will replace the sharp water/hexane boundary with diffuse water/IPA and IPA/hexane interfaces. If made of appropriate thickness, the IPA will maintain the one-phase condition through the shaping of the fluids, then diffuse away sufficiently the water/hexane interface to be reestablished.

Production of Fibers with Lateral Variation in Composition.

More than one polymerizable material can be incorporated into the same core, resulting in fibers with multiple compositions in a predefined conformation. FIG. 18 shows a cross-section through a channel where several concentric flow streams have been created. Inclusion of polymerizable materials in the flow stream would produce a fiber with several concentric layers. A concentric configuration could be particularly useful in situations where a fiber is wanted with differing bulk and surface properties. It is expected that a wide variety of configurations of two or more polymerizable materials can be constructed using the shaping structures. FIG. 26 shows just a few possible conformations that can be created. The lateral composition does not have to be discrete. Elements placed upstream of the sheathing can be designed to create continuous gradients as well, such as those found in gradient index fibers. Alternatively, merger of multiple streams prior to polymerization can be used to create lateral gradients.

Gradients can exist in one or more components of the core and/or sheath. For example, gradients can exist in the concentration of crosslinker, ions, and/or polymerizable material. More than one gradient can exist simultaneously.

Not all of the structures in the shaped streams need to be something that ultimately hardens. For example a hollow fiber could be made that is filled with a liquid. Because structure can also be changed longitudinally, the lumen can be pinched off periodically, so that a cut in the fiber does not cause its entire length to drain. Applications for this kind of structure would include drug release, contaminant sequestration, phase-change thermal fabrics, etc. The structures could also be deliberately drained after fiber production, thereby creating voids. Large voids could be used as tubing, while multiple smaller voids have a possible application in photonic materials. It should also be noted that unlike classical extrusion technologies, the voids can be made to split or recombine by the same mechanism used to make fibers that split and recombine (as noted above with regard to multiple fibers from a single channel).

Production of Fibers with Residual Stresses (Curly Fibers).

Figure 27:
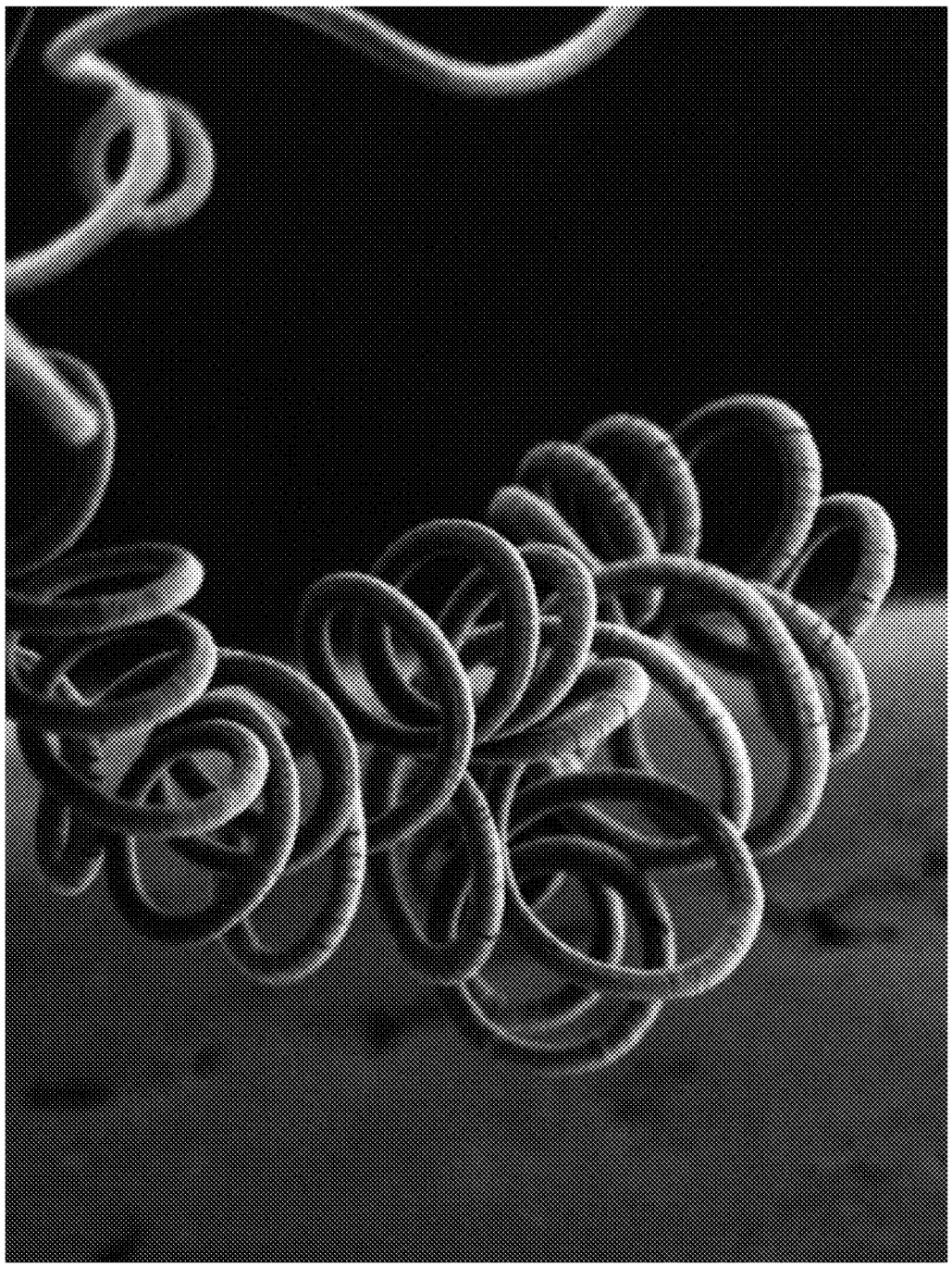
FIG. 27 shows a curly fiber.
Figure 28:
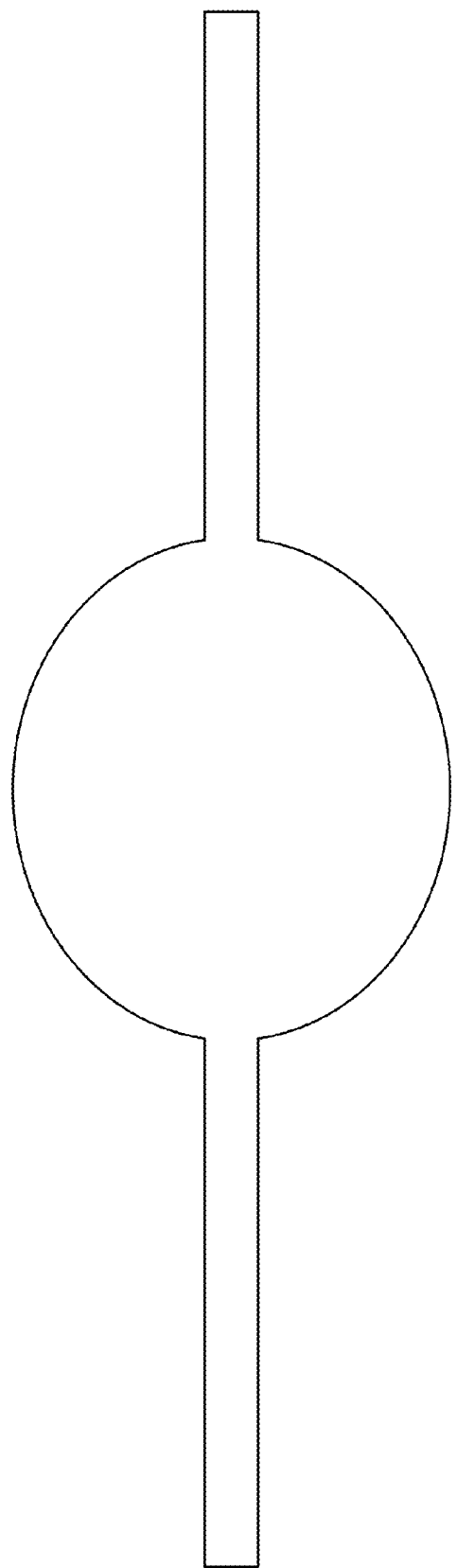
FIG. 28 shows a schematic cross-section of a fiber with high surface area.

Another layer of structure can be added to the fiber by introduction of residual stresses. Many polymers contract during curing. By using the ability to make fibers of differing lateral compositions, one could deliberately engineer the contraction to cause the fibers to curl. Differential curing could also be induced by chemical, light or other gradients. FIG. 27 shows a fiber where stresses were introduced, most likely due to a light shining on one side. Prestressed fibers are not limited to round shapes. A fiber could be produced with a central core and one or more long "wings" extending from the core, seen in FIG. 28. If the core is designed to contract during curing, the wings will develop a scalloped or frilled pattern. Such a fiber would have a higher surface area per unit length, making it well suited for filtering or catalytic applications.

Deliberate Buckling, Breaking, or Other Effects of Applying Forces on Nascent Fibers.

Figure 29:
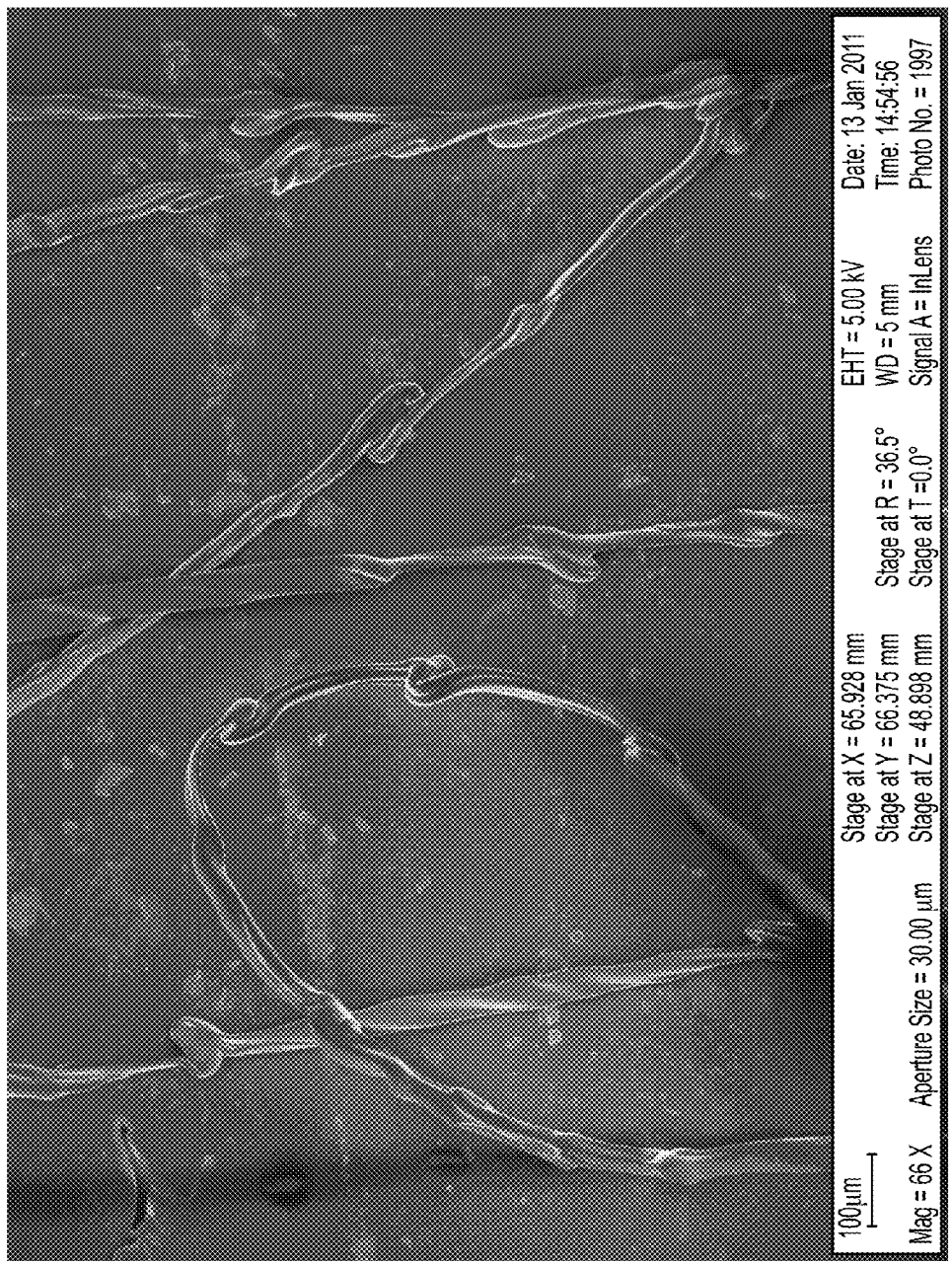
FIG. 29 shows a fiber exhibiting regular viscous buckling.

As the material comprising the fiber hardens, it can be subjected to forces that affect its ultimate molecular or gross structure. One example can be seen in FIG. 29. When a viscous fluid stream is forced to decelerate, it can buckle upon itself as seen here. This viscous buckling can take other forms, including the spiral motion of a stream of syrup as it lands on a surface. A similar behavior could be used to create helical fibers. The forming fibers could also be exposed to stretching or bending. If the material is ductile enough, this could simply help to align polymer fibers or have other desirable effects on the composition of the fiber. If a more brittle material is used (e.g. sol gels), the result could be the break-up of the fiber into rods of regular size, shape, and aspect ratio.

Printing with Sheathed Flow.

A partially polymerized stream can be directed onto a surface while the surface is moved relative to the stream, or vice versa. If polymerization is incomplete at the time the fiber is laid down, there is a tendency for the fiber to adhere and conform to the substrate on which is it being laid. Preferably under computer control, patterns can be laid down on a surface, and multiple levels of a fibers could be laid down to print three-dimensional objects, with the resolution of the object set by the diameter of the fiber.

Tissue Engineering with Animal Cells

Hydrodynamic focusing core/sheath flow as described above may be used to create polymer fibers containing cells from mammals or other animals. The fibers can be comprised of one or more layers concentrically arranged around a central lumen (derived from the core stream), which is optionally hollow or filled. In the case of a hollow lumen, the core stream would include material that is not polymerized, whereas including polymerizable material in the core stream could create a lumen filled with polymer to form a "solid" fiber. The cells can be inside the lumen, embedded in one or more layers, and/or adherent to the outside surface of the fiber. The cells in each layer may be the same or different in origin, with any type of cell found in an animal a candidate for use in this technique, including cells from mammals, birds, fish, reptiles, amphibians, insects, etc. The materials in the polymer are preferably biocompatible. Other components beyond cells and pre-polymer can be included in the flows and thus be incorporated in the resulting fibers, for example factors to modify cell growth, adhesion, and/or differentiation. It is also possible to incorporate nucleic acids (such as RNA or single or double stranded DNA fragments) in the polymer matrix. These nucleic acid moieties could be used to bind proteins or peptides or as templates for replication or functionalization. Furthermore, materials can be selected so that 90% or more of the polymer in the fiber is degraded by the cells and replaced with extracellular matrix, or only certain of the concentric layers may be designed for such biodegradation. The cell-containing fibers can mimic natural structures such as capillaries, blood vessels, tissue ducts, or nerves. Thickness of individual polymer layers is limited primarily in order to allow for diffusion of oxygen and nutrients to the cells.

Microchannels with grooved structures in the top and bottom of the channel can be designed to use a phase-matched sheath fluid to focus a polymerizable core stream into a pre-determined shape without mixing, as described in members of this patent family and publications of inventors thereof, including Boyd, D. A., A. R. Shields, J. Naciri, and F. S. Ligler (2012) "Hydrodynamic shaping, polymerization, and subsequent modification of thiol click fibers," *ACS Appl. Mater. Interfaces*, recently accepted manuscript, DOI: 10.1021/am3022834; Shields, A. R., A. L. Thangawng, C. M. Spillmann, J. Naciri, P. B. Howell, and F. S. Ligler (2012) "Hydrodynamically directed multiscale assembly of shaped polymer fibers," *Soft Matter* 8, 6656-6660; Thangawng, A. L., P. B. Howell, C. M. Spillman, J. Naciri, and F. S. Ligler (2011) "UV polymerization of hydrodynamically shaped fibers," *Lab Chip* 11, 1157-1160; and Thangawng, A. L., P. B. Howell, J. J. Richards, J. S. Erickson, and F. S. Ligler (2009) "A simple sheath-flow microfluidic device for micro/nanomanufacturing: fabrication of hydrodynamically shaped polymer fibers," *Lab Chip* 9, 3126-3130. The cross-sectional dimensions can be determined by the relative flow rates of the sheath and core. Using multiple fluid additions, successive layers of fluids can be wrapped around the core, as shown in FIG. 18.

For use of animal cells during the fabrication process, it is desirable that any photopolymerization of the prepolymer material be accomplished rapidly (with minimal if any damage to the cells) and that the flows be under moderate pressure (to reduce shear stresses on the cells). The engineered material used in the experiments described here was a bio/synthetic hydrogel composed of gelatin methacrylamide (GelMA) and poly(ethylene glycol) (PEG). By modifying the gelatin with methacrylate groups and PEG with thiol or alkyne groups, a biocompatible hydrogel was formed that can be rapidly crosslinked by mild UV exposure and had adjustable physiochemical properties. The GelMA was selected for the presence of the peptide RGD known to exhibit binding sites that facilitate cellular ingrowth and extracellular matrix formation. The PEG was chosen to provide mechanical support during formation of the hollow fibers and matrix remodeling (e.g. cell-induced degradation of the gelatin and replacement with extracellular matrix). The hydrogel proved to be biocompatible for both cell adherence and encapsulation of endothelial cells. Other biocompatible materials can also be used as long as the conditions for polymerization or casting do not damage the cells.

Polymers may include proteins, peptides, collagen, agarose, polyelectrolytes, chitosan, gelatin, hyaluronic acid, heteropolysaccharides, polyethylene glycol, hydroxyethylmethacrylate (HEMA), gelatin methacrylamide (GelMA), poly(methyl methacrylate) (PMMA), poly(lactic-co-glycolic acid) (PLGA), polylactic acid (PLLA), derivatives of any of these, and combinations thereof.

Figure 32:
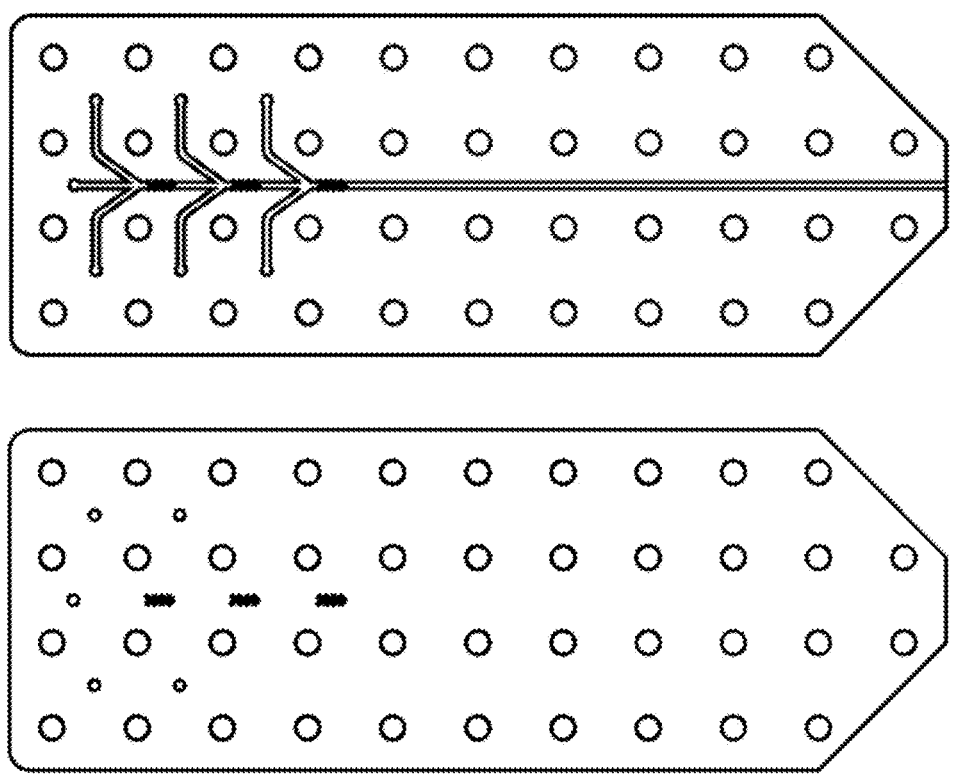
FIG. 32 illustrates the cover and substrate layers of a sheath flow device used to manufacture hollow or solid multi-layer polymer fibers. This device operates similarly to the device presented in FIG. 30, except sheath is introduced along with a corresponding set of chevrons that serve to add a third layer. The cross-sectional areas of flows are produced from two sets of chevron shaping features, three sets of chevron shaping features, and two sets of striped shaping features.
Figure 33:
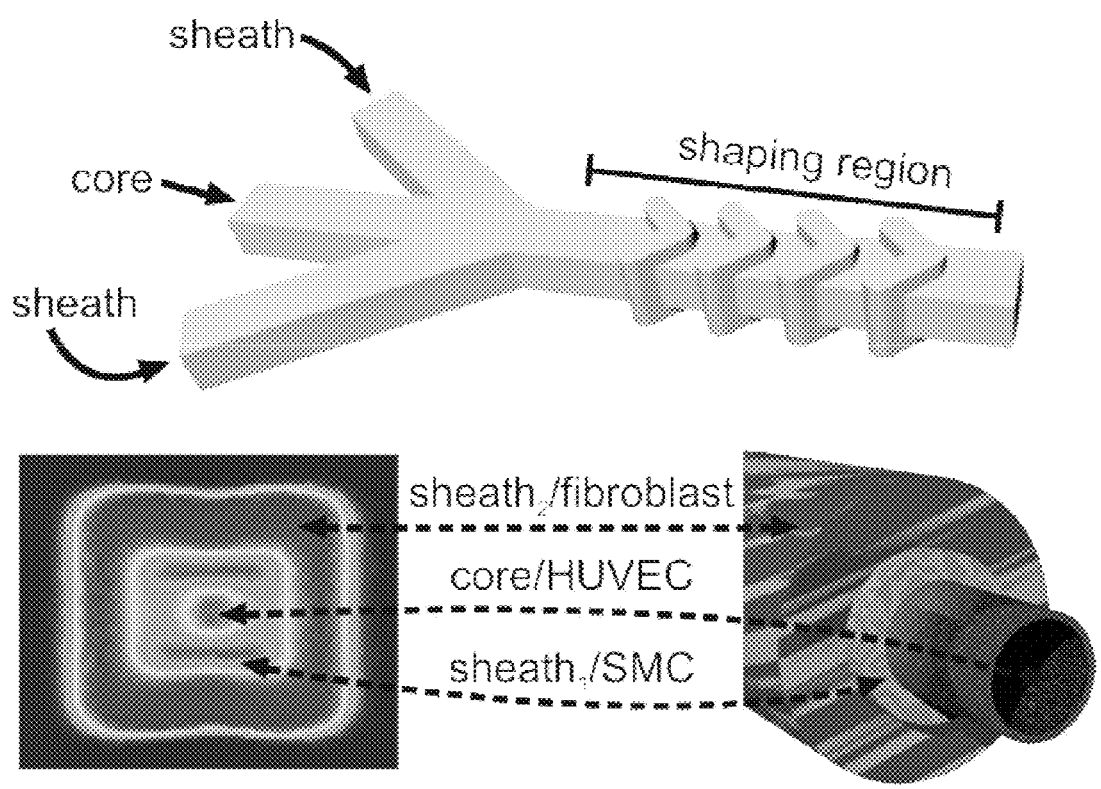
FIG. 33 shows a hydrodynamic shaping device with a representative computational model of the layered fluid flow. Discrete regions of flow will correlate to micro-blood vessel layers. Each layer requires a segment of the microfluidic channel to incorporate an additional hydrodynamic shaping device.
Figure 34:
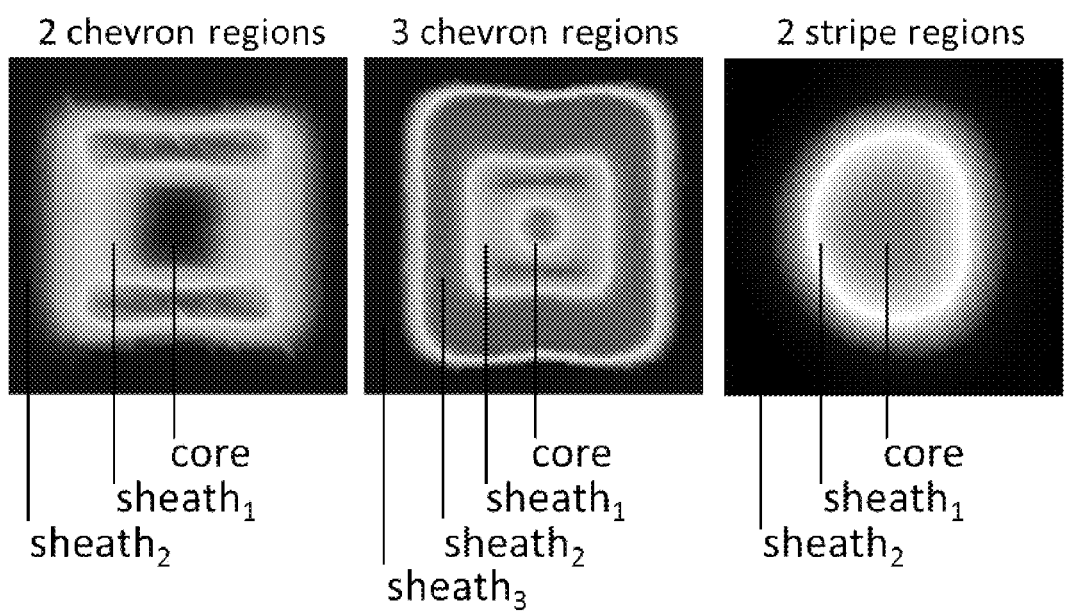
FIG. 34 shows computational fluid dynamic simulations of hollow tubes that can be fabricated using hydrodynamic focusing with fluid transporting structures in the top and bottom of microchannels. Use of either stripes or chevrons will produce multilayered fibers. Additional sets of chevrons produce additional concentric layers.

By utilizing an additional set of hydrodynamic shaping features in the top and bottom of the channel as seen in FIG. 32, the biocompatible hydrogel precursors are directed into concentric layers and photopolymerized in situ. To make a two-layer hollow tube, the first "core fluid" is not polymerizable. The initial stage of the device focuses the nonpolymerizable core, while the second stage focuses the prepolymer designed to become the inner layer of the hollow fiber. Unlike the example depicted in FIGS. 30 and 31, however, the sheath fluid introduced in the second stage is also polymerizable. In the third stage, the first three solutions are completely ensheathed in a fourth, nonpolymerizable solution. The concentric polymerizable fluids are then polymerized after passing through the final set of fluid transporting structures, preferably using broad-spectrum ultraviolet light ($\leq 10$ mW/cm$^2$). The diameter of the lumen and the thickness of the layers in the hollow fiber is a function of the relative fluid flow rates of each of the fluids introduced into the microfluidic channel. FIG. 33 shows computational fluid dynamic models of the lumen and the polymerizable layers that would be obtained using variations in shaping features and in the flow-rate ratios and cross-sectional areas of flows produced from two sets of chevron shaping features, three sets of chevron shaping features, and two sets of striped shaping features. The flow-rate ratios are consistent in all the shaping simulations. Exemplary flow-rate ratios that provided good results were core: sheath$_n$: sheath$_{n+1}$ such that each subsequent layer is 4 times the flow rate of the previous layer. For example, a core flow with 3 sheaths would have flow-rate ratios of 1:4:16:64 using this formula, however variations are possible.

Cells can be included in any of the streams during the fabrication process, depending on the desired configuration of the model system. Blood vessels include endothelium on the inner layer, smooth muscle cells in the primary wall of the vessel, and a surrounding layer including fibroblasts and extracellular matrix, as depicted in FIG. 33. During the fabrication of a model blood vessel, endothelial cells are included in the first nonpolymerizable core fluid, smooth muscle cells are included in the prepolymer used as the first sheath fluid, and fibroblasts are included in the second sheath prepolymer fluid. The nonpolymerizable fluids included cell culture media with unmodified gelatin or PEG to increase the viscosity and match it to the viscosity of the polymerizable fluids. The bio/synthetic hydrogel employed to produce the multi-walled microtubes is seeded with cells before injection into the microfluidic shaping device. The luminal fluid contains Human Umbilical Vein Endothelial Cells (HUVEC) that can attach to the interior surface of the micro-blood vessel. The first prepolymer fluid for making the interior elastic layer incorporates Primary Coronary Artery Smooth Muscle Cells (PCSMC). The prepolymer for the external layer incorporates Human Dermal Fibroblasts. The shaping features focus the cell-containing flows into the respective zones to produce the multi-walled microtubes. Polymerization is sufficiently brief that cell damage does not occur. The generated micro-blood vessels are collected directly into sterile cell culture medium for individual study or for incorporation into tissue-on-chip model systems.

This microfabrication approach is modular, so that additional inlets and shaping features can be appended to the design to produce any number of concentric polymer layers. The previously tested GelMA-PEG hydrogel has been used to form the microtubes and has proven biocompatibility and mechanical strength. The flexible photochemistry also allows for the inclusion of instructive biological components, a popular methodology in tissue engineering to encourage cellular proliferation. [Lutolf M P, Hubbell J A. "Synthetic biomaterials as instructive extracellular microenvironments for morphogenesis in tissue engineering," *Nature Biotechnol.* 2005; 23(1):47-55; Geckil H, Xu F, Zhang X H, Moon S, Demirci U. "Engineering hydrogels as extracellular matrix mimics," *Nanomedicine-UK.* 2010; 5(3):469-484.]

In addition to including cells in the prepolymer layers, cells can be included in the nonpolymerizable fluids. In the experiment described above, endothelial cells were included in the interior wall of the tubule. Flow introduced subsequently through the hollow tube will encourage the formation of continuous monolayers on the inner wall of the tubule. Similar results would be obtained with renal epithelial cells in a matrix, mimicking the kidney basement membrane. Cells could also be included with the outer sheath layer that would attach to the outer surface of the tubule as it is formed to provide an even more defined organization of multiple cell types.

Incorporation of the micro-blood vessels into tissue-on-chip systems provides for biomimetic delivery of nutrients and growth factors and for the creation of biological gradients similar to those naturally occurring as different cell types are organized in complex tissues in vivo. In one example, the micro-blood vessels are used to study intramembranous ossification. Hierarchically-layered microfabricated blood vessels are engineered through the combined use of hydrodynamic shaping and in situ polymerization. These micro-blood vessels with heterotypic cellular architecture are fabricated with diameters ranging from 5 μm to 1 mm and mean wall thickness between 0.5 μm and 500 μm. The micro-blood vessels are integrated into the microchip bioreactor that is schematically shown in FIG. 33. Mesenchymal stem cells in a biocompatible hydrogel are introduced into the chamber surrounding the micro-blood vessels. Unlike other microchip tissue models [Gibbons M C, Foley M A, O'Halloran-Cardinal K. "Thinking inside the box: Keeping tissue-engineered constructs in vitro for use as preclinical models. Tissue Engineering: Part B,". 2012; 19(1):17], the human vascularized bone model described here incorporates both a free standing vasculature network and three-dimensional cell scaffold. The incorporated vasculature provides the opportunity to model the mechanical and material transport properties that dictate endothelial-mesenchymal stem cell interactions during intramembranous ossification. Analysis of both vasculogenesis and osteogenesis will provide a biologically relevant human vascularized tissue model to investigate bone development and healing This technique can also provide a multi-scale approach to musculoskeletal tissue engineering that combines nanoscale molecular alignment, microengineered tissues and biomimetic scaffolds. Engineered tissues for musculoskeletal repair are often limited by a lack of vascularity, inability to replicate the complex bone microarchitecture and insufficient scaffold mechanical strength. Based on recent findings that unique material compositions and multiple cell types can be incorporated in a single micron-sized fiber via the hydrodynamic focusing described here, concentric-layered hydrogel constructs with spatially varying biomaterial layers can be used for organizing a mixed-cell population into a complex muscle fiber or osteon. The concentric geometry of both muscle fibers and osteon can be achieved.

Anatomically and functionally, fibrous muscle tissue consists of spatially distinct regions which each contain a distinct resident cell type and series of matrix tissue. Each zone is characterized by unique extra-cellular matrix compositions, mechanical properties and cellular organization. Osteon, the functional unit of compact bone, are cylindrical structures that are typically several millimeters long and around 0.2 mm in diameter. Each osteon consists of concentric layers, or lamellae, of compact bone tissue that surround a central canal. By concentrically layering biomimetic materials, microengineered muscle fiber and osteon-like units can be formed. This will result in mineralized vascular tissues with controlled architectures on a variety of functional and physiologically relevant scales. The combined use of microfluidic shaping and in situ polymerization can produce multi-layer fibers with diameters ranging from 10 μm to 1 mm containing different cell types. The fibers can be encased in an additional cell-free layer less than 10 μm thick to replicate the membranous structures that encapsulate a muscle fiber or osteon. Microfluidic channels similar to those in FIGS. 30 and 32 include additional fluid transporting regions to focus pre-tissue solutions into the respective zones of a multi-layer fiber. Size-control in this regime is necessary to reproduce individual muscle fibers. Groups of fibers can be bundled into large muscular tissue models which contain both sarcolemma and endomysium.

Figure 35:
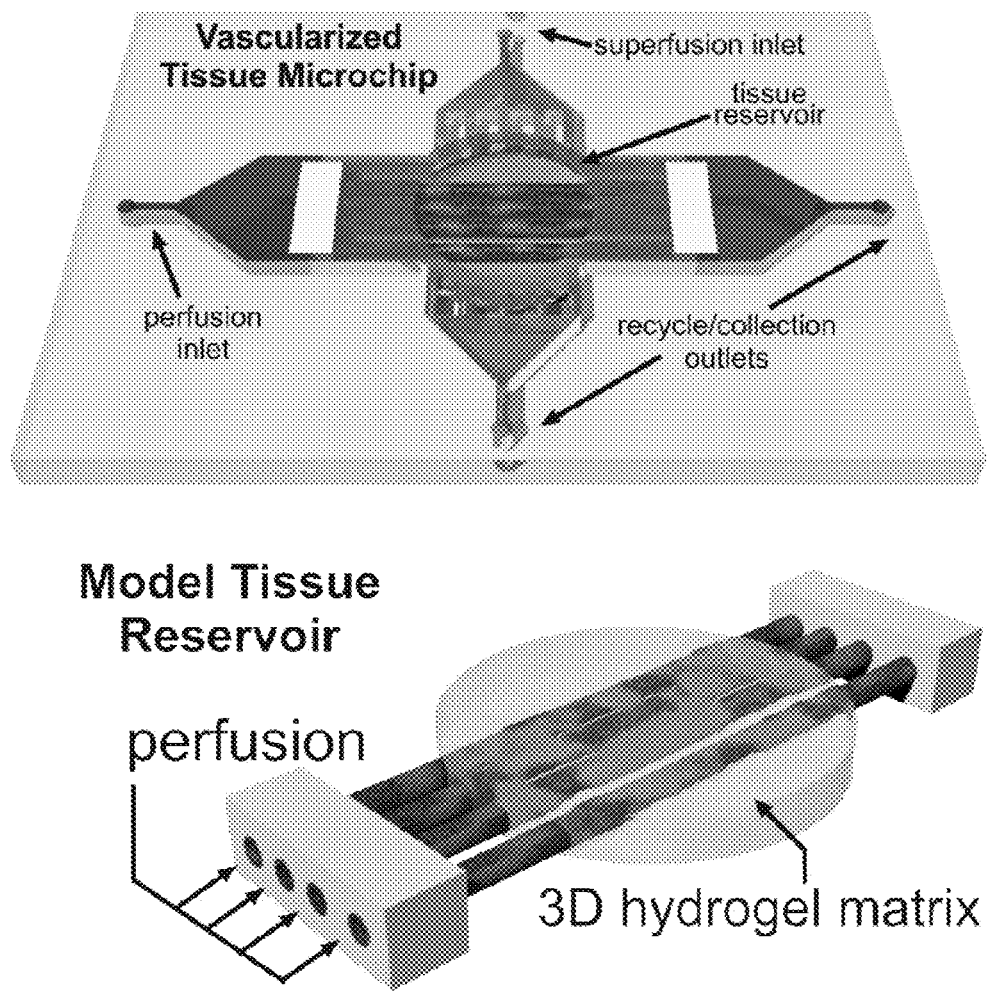
FIG. 35 illustrates a model issue microchip vascularized with the micro-blood vessels that can be utilized for both mechanical and physiological analyses. The integrated tissue reservoir incorporates a 3-dimensional hydrogel matrix to support vasculogenesis and 3-dimensional culturing of osteogenic cells.

FIG. 35 illustrates a model tissue microchip vascularized with the fibers configured as micro-blood vessels; the chip can be utilized for both biomechanical and physiological analyses. The integrated tissue reservoir incorporates a 3-dimensional hydrogel matrix to support vasculogenesis and 3-dimensional culturing of osteogenic cells. Such a tissue model can incorporate micro-vessels or ducts or nerves embedded in it as described above, and be used with 3-dimensional cultures of a wide variety of tissue types. Inlet ports and outlet ports can direct fluid through a hollow fiber, and/or provide nutrients either through the fiber itself or to a surrounding hydrogel matrix.

Each document mentioned herein is incorporated by reference. Furthermore, one of ordinary skill in the art will understand that many modifications and variations of the present invention are possible in light of the above teachings. It is therefore to be understood that, within the scope of the appended claims, the invention may be practiced otherwise than as specifically described.

What is claimed is:

1. A fiber comprising:
   at least two concentric layers of polymer surrounding a central lumen, and
   living animal cells disposed within the at least two concentric layers of polymer and optionally within the lumen, wherein different animal cells are disposed in different layers of polymer,
   wherein the fiber has an outer diameter of between 5 and 8000 microns and wherein each individual layer of polymer has a thickness of between 0.1 and 250 microns, and
   wherein the fiber is in a condition of having been generated via sheath flow.

2. The fiber of claim 1, wherein the fiber is hollow and the lumen is substantially free of polymer.

3. The fiber of claim 1, wherein the lumen is filled with a polymer and optionally comprises living animal cells.

4. The fiber of claim 1, further comprising cells adhered to an exterior surface of said fiber.

5. The fiber of claim 1, wherein the fiber is free of attachment along a surface.

6. The fiber of claim 1, wherein the polymer in at least one of said one or more layers is biodegradable.

7. The fiber of claim 1, configured as a blood vessel, tissue duct, or nerve.

8. The fiber of claim 1, wherein the polymer in at least one of said one or more layers comprises a material is selected from the group consisting of collagen, agarose, polyelectrolytes, chitosan, gelatin, polyethylene glycol, peptides, derivatives thereof, and combinations thereof.

9. The fiber of claim 1, wherein at least one of said one or more layers further comprises a nucleic acid and/or a factor to modify cell growth, adhesion, and/or differentiation.

10. The fiber of claim 1, wherein the fiber is configured for transport of molecules, particles, and/or cells into the fiber from an environment outside the fiber; and/or to transport molecules, particles, and/or cells from within the fiber to the environment outside the fiber.

* * * * *